(12) United States Patent
Akireddy et al.

(10) Patent No.: US 10,421,745 B2
(45) Date of Patent: Sep. 24, 2019

(54) SALT FORMS OF (R)-5-((E)-2-PYRROLIDIN-3-YLVINYL) PYRIMIDINE

(71) Applicant: Oyster Point Pharma, Inc., Princeton, NJ (US)

(72) Inventors: Srinivasa Rao Akireddy, Winston-Salem, NC (US); Balwinder Singh Bhatti, Winston-Salem, NC (US); Timothy J. Cuthbertson, Winston-Salem, NC (US); Gary Maurice Dull, Lewisville, NC (US); Craig Harrison Miller, Winston-Salem, NC (US); Joseph Pike Mitchener, Jr., Winston-Salem, NC (US); Julio A. Munoz, Walnut Cove, NC (US); Pieter Albert Otten, King, NC (US)

(73) Assignee: Oyster Point Pharma, Inc., Princeton, NJ (US)

( * ) Notice: Subject to any disclaimer, the term of this patent is extended or adjusted under 35 U.S.C. 154(b) by 0 days.

(21) Appl. No.: 15/962,982

(22) Filed: Apr. 25, 2018

(65) Prior Publication Data
US 2019/0071428 A1 Mar. 7, 2019

Related U.S. Application Data

(63) Continuation of application No. 15/354,832, filed on Nov. 17, 2016, now Pat. No. 9,981,949, which is a continuation of application No. 14/832,030, filed on Aug. 21, 2015, now abandoned, which is a continuation of application No. 14/074,147, filed on Nov. 7, 2013, now Pat. No. 9,145,396, which is a continuation of application No. 13/129,898, filed as application No. PCT/US2009/066078 on Nov. 30, 2009, now Pat. No. 8,604,191.

(60) Provisional application No. 61/118,796, filed on Dec. 1, 2008.

(51) Int. Cl.
C07D 403/06 (2006.01)
C07C 59/255 (2006.01)
A61K 31/4025 (2006.01)
C07C 59/265 (2006.01)

(52) U.S. Cl.
CPC ........ *C07D 403/06* (2013.01); *A61K 31/4025* (2013.01); *C07C 59/255* (2013.01); *C07C 59/265* (2013.01)

(58) Field of Classification Search
CPC ............. C07D 403/06; A61K 31/4025
USPC ........................ 544/242; 514/256
See application file for complete search history.

(56) References Cited

U.S. PATENT DOCUMENTS

| | | |
|---|---|---|
| 4,649,041 A | 3/1987 | Peters et al. |
| 4,950,140 A | 8/1990 | Pflaumer et al. |
| 5,106,851 A | 4/1992 | Turconi et al. |
| 5,189,041 A | 2/1993 | Berger et al. |
| 5,378,474 A | 1/1995 | Morella et al. |
| 5,583,140 A | 12/1996 | Bencherif et al. |
| 5,597,919 A | 1/1997 | Dull et al. |
| 5,604,231 A | 2/1997 | Smith et al. |
| 5,795,909 A | 8/1998 | Shashoua et al. |
| 5,852,041 A | 12/1998 | Cosford et al. |
| 5,853,696 A | 12/1998 | Elmaleh et al. |
| 5,952,339 A | 9/1999 | Bencherif et al. |
| 5,969,144 A | 10/1999 | London et al. |
| 6,290,994 B1 | 9/2001 | Lazaro Flores et al. |
| 6,310,043 B1 | 10/2001 | Bundle et al. |
| 6,602,902 B2 | 8/2003 | Shashoua et al. |
| 6,761,903 B2 | 7/2004 | Chen et al. |
| 6,872,827 B2 | 3/2005 | Webb et al. |
| 6,965,027 B2 | 11/2005 | Flanagan et al. |
| 7,098,331 B2 | 8/2006 | Schmitt et al. |
| 7,714,001 B2 | 5/2010 | Schmitt et al. |
| 8,063,068 B2 | 11/2011 | Schmitt et al. |
| 8,067,443 B2 | 11/2011 | Genevois-Borella et al. |
| 8,604,191 B2 | 12/2013 | Akireddy et al. |
| 8,633,222 B2 | 1/2014 | Schmitt et al. |
| 9,145,396 B2 | 9/2015 | Akireddy et al. |
| 9,981,949 B2 | 5/2018 | Akireddy et al. |
| 2006/0223820 A1 | 10/2006 | Brand et al. |
| 2007/0032481 A1 | 2/2007 | Dvorak et al. |
| 2007/0173509 A1 | 7/2007 | Buzard et al. |
| 2016/0046609 A1 | 2/2016 | Akireddy et al. |

FOREIGN PATENT DOCUMENTS

| | | |
|---|---|---|
| EA | 014714 | 2/2011 |
| EA | 019240 | 2/2014 |
| RU | 2011127004 A | 7/2013 |
| RU | 2507197 | 2/2014 |
| WO | WO-1994/008992 A1 | 4/1994 |
| WO | WO-1996/031475 A2 | 10/1996 |
| WO | WO-1996/040682 A1 | 12/1996 |
| WO | WO-1998/025619 A1 | 6/1998 |
| WO | WO-2004/078752 A1 | 9/2004 |
| WO | WO-2006/113837 A2 | 10/2006 |
| WO | WO-2006/133498 A1 | 12/2006 |

(Continued)

OTHER PUBLICATIONS

Adeyeye, Moji, ed., "Preformulation in Solid Dosage Form Development," Informa Healthcare, Chapter 2.3, pp. 63-80 (2008).

(Continued)

*Primary Examiner* — Deepak R Rao

(74) *Attorney, Agent, or Firm* — Cooley LLP

(57) ABSTRACT

The present invention relates to the stereospecific synthesis of (R)-5-((E)-2-pyrrolidin-3-ylvinyl)pyrimidine, its salt forms, and novel polymorphic forms of these salts.

14 Claims, 8 Drawing Sheets

(56) References Cited

FOREIGN PATENT DOCUMENTS

| WO | WO-2008/157365 A2 | 12/2008 |
|---|---|---|
| WO | WO-2010/065443 A1 | 6/2010 |
| WO | WO-2010/065447 A2 | 6/2010 |
| WO | WO-2017/177024 A1 | 10/2017 |

OTHER PUBLICATIONS

Arneric, S. P., et al., "Cholinergic Channel Modulators as a novel Therapeutic Strategy for Alzheimers Disease," Exp. Opin. Invest. Drugs 5(1): 79-100 (1996).
Arneric, S.P., et al., "Preclinical Pharmacology of ABT-418: A Protypical Cholinergic Channel Activator for the Potential Treatment of Alzheimer's Disease," CNS Drug Rev. 1(1): 1-26 (1995).
Bannon, A.W., et al., "Broad-Spectrum, Non-Opiod Analgesic Activity by Selective Modulation of Neuronal Nicotinic Acetylcholine Receptors," Science 279: 77 (1998).
Bastin et al., "Salt Selection and Optimisation Procedures for Pharmaceutical New Chemical Entities," Organic Process Research and Development 2000, 4, 427-435.
Chiari, A., et al., "Sex Differences in Cholinergic Analgesia I," Anesthesiology 91: 1447 (1999).
Damaj, M.I., et al., "Antinociceptive and Pharmacological Effects of Metanicotine, a Selective Nicotinic Agonist," J. Pharmacol. Exp. Ther. 291: 390 (1999).
Eoff et al., "Optimal Treatment of Chronic Constipation in Managed Care: Review and Roundtable Discussion," Journal of Managed Care Pharmacy, vol. 14, No. 9-a, pp. S1-S17 (Nov. 2008).
Extended European Search Report dated Dec. 4, 2017, by the European Patent Office for Application No. 17179369.8, filed Jun. 26, 2017, 8 pages.
Final Office Action issued by the United States Patent and Trademark Office for U.S. Appl. No. 14/074,147, dated Jan. 2, 2015, 7 pages.
Gould, International J. of Therapeutics 33, 201 (1986).
Haynes et al: "Occurrence of Pharmaceutically Acceptable Anions and Cations in the Cambridge Structural Database", Cambridge, UK, May 16, 2005, 10 pages.
Holladay, M.W., et al., "Neuronal Nicotinic Acetylcholine Receptors as Targets for Drug Discovery," J. Med. Chem. 40(28): 4169-94 (1997).
International Search Report and Written Opinion dated Mar. 30, 2010, by the International Searching Authority for Application No. PCT/US2009/066078, filed Nov. 30, 2009, 15 pages.
Lakhan et al., Anti-inflammatory effects of nicotine in obesity and ulcerative colitis, Journal of Translational Medicine, 9:129, pp. 1-10 (2011).
Lavand'homme and Eisenbach, "Sex Differences in Cholinergic Analgesia II," Anesthesiology 91: 1455 (1999).
Lippiello, P.M., et al., "RJR-2403: A Nicotinic Agonist with CNS Selectivity II. In Vivo Characterization," J. Pharmacol. Exp. Ther. 279: 1422 (1996).
Liu, Rong, ed., "Water-Insoluble Drug Formulation," (CRC Press, 2008) Chapter 15 pp. 417-435.
Morris, et al., "An Integrated Approach to the Selection of Optimal Salt form for a New Drug Candidate," International Journal of Pharmaceutics 105 (1994) 209-217.
Non-Final Office Action issued by The United States Patent and Trademark Office for U.S. Appl. No. 13/129,898, dated May 10, 2013, 17 pages.
Non-Final Office Action issued by The United States Patent and Trademark Office for U.S. Appl. No. 14/074,147, dated Jul. 23, 2014, 11 pages.
Non-Final Office Action issued by The United States Patent and Trademark Office for U.S. Appl. No. 14/832,030, dated May 18, 2016, 12 pages.
Non-Final Office Action issued by The United States Patent and Trademark Office for U.S. Appl. No. 15/354,832, dated Jul. 26, 2017, 10 pages.
Notice of Allowance issued by The United States Patent and Trademark Office for U.S. Appl. No. 13/129,898, dated Aug. 14, 2013, 6 pages.
Notice of Allowance issued by The United States Patent and Trademark Office for U.S. Appl. No. 14/074,147, dated May 22, 2015, 6 pages.
Notice of Allowance issued by The United States Patent and Trademark Office for U.S. Appl. No. 15/345,832, dated Feb. 13, 2018, 4 pages.
Notice of Allowance issued by The United States Patent and Trademark Office for U.S. Appl. No. 15/354,832, dated Jan. 26, 2018, 7 pages.
Serajuddin, "Salt Formation to Improve Drug Solulability," Advanced Drug Delivery Reviews 59 (2007) 603-616.
Swarbrick et al., eds., Encyclopedia of Pharmaceutical Technology 13 (Marcel Dekker, NY 1996) pp. 453-499.
Talley, "Functional gastrointestinal disorders as a public health problem," Neurogastroenterol Motil (2008) 20 (Suppl. 1), pp. 121-129.
Tracey, K.J., "The Inflammatory Reflex," Nature 420: 853-9 (2002).
Villemagne, V.L., et al., "Nicotine and Related Compounds as Pet and Spect Ligands," Neuronal Nicotinic Receptors: Pharmacology and Therapeutic Opportunities, 235-250 (1998).
Williams, A. W., et al., "Broad-Spectrum, Non-Opiod Analgesic Activity by Selective Modulation of Neuronal Nicotinic Acetylcholine Receptors," Drug News Perspec. 7(4): 205 (1994).
U.S. Appl. No. 16/091,830, filed Oct. 5, 2018, for Ackermann et al.

SALT FORMS OF (R)-5-((E)-2-PYRROLIDIN-3-YLVINYL)PYRIMIDINE

CROSS REFERENCE

The present application is a continuation of U.S. application Ser. No. 15/354,832, filed Nov. 17, 2016, now patented U.S. Pat. No. 9,981,949, which is a continuation of U.S. application Ser. No. 14/832,030, filed Aug. 21, 2015, now abandoned, which is a continuation of U.S. application Ser. No. 14/074,147, filed Nov. 7, 2013, now patented U.S. Pat. No. 9,145,396, which is a continuation of U.S. application Ser. No. 13/129,898, filed Aug. 1, 2011, now patented U.S. Pat. No. 8,604,191, which is a § 371 of International Application Number PCT/US09/66078, filed Nov. 30, 2009, which claims benefit to U.S. Provisional Application Ser. No. 61/118,796, filed Dec. 1, 2008, each of which is incorporated by reference in its entirety.

FIELD OF THE INVENTION

The present invention relates to a stereospecific synthesis of (R)-5-((E)-2-pyrrolidin-3-ylvinyl)pyrimidine, its salt forms, and novel polymorphic forms of these salts. The present invention also includes pharmaceutical compositions of these salt forms as well as methods for treating a wide variety of conditions and disorders, including pain, inflammation, and conditions and disorders associated with dysfunction of the central and autonomic nervous systems.

BACKGROUND OF THE INVENTION

The compound (R)-5-((E)-2-pyrrolidin-3-ylvinyl)pyrimidine is a neuronal nicotinic receptor (NNR) agonist with selectivity for the α4β2 nicotinic subtype over other nicotinic subtypes, for example, the α7 subtype, the ganglionic, and the muscle subtypes. (R)-5-((E)-2-pyrrolidin-3-ylvinyl)pyrimidine provides benefits in the treatment or prevention of central nervous system (CNS) disorders and pain.

(R)-5-((E)-2-pyrrolidin-3-ylvinyl)pyrimidine has the following structural formula:

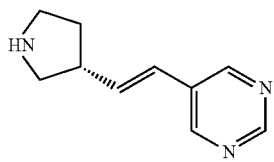 [SMILES: C(=C\[C@H]1CCNC1)/c1cncnc1]

The commercial development of a drug candidate such as (R)-5-((E)-2-pyrrolidin-3-ylvinyl)pyrimidine involves many steps, including the development of a cost effective synthetic method that is adaptable to a large scale manufacturing process. Commercial development also involves research regarding salt forms of the drug substance that exhibit suitable purity, chemical stability, pharmaceutical properties, and characteristics that facilitate convenient handling and processing. Furthermore, compositions containing the drug substance should have adequate shelf life. That is, they should not exhibit significant changes in physicochemical characteristics such as, but not limited to, chemical composition, water content, density, hygroscopicity, and solubility upon storage over an appreciable period of time. Additionally, reproducible and constant plasma concentration profiles of drug upon administration to a patient are also important factors.

Solid salt forms are generally preferred for oral formulations due to their tendency to exhibit these properties in a preferential way; and in the case of basic drugs such as (R)-5-((E)-2-pyrrolidin-3-ylvinyl)pyrimidine, acid addition salts are often the preferred salt form. However, different salt forms vary greatly in their ability to impart these properties, and such properties cannot be predicted with reasonable accuracy. For example, some salts are solids at ambient temperatures, while other salts are liquids, viscous oils, or gums at ambient temperatures. Furthermore, some salt forms are stable to heat and light under extreme conditions and others readily decompose under much milder conditions. Thus, the development of a suitable acid addition salt form of a basic drug for use in a pharmaceutical composition is a highly unpredictable process.

The synthesis of 5-((E)-2-pyrrolidin-3-ylvinyl)pyrimidine and its hemi-galactarate salt, its separation by chiral chromatography into optical isomers and the galatarate salts of the isomers are disclosed in published WO 04/078752 and U.S. Pat. No. 7,098,331, each of which is incorporated by reference. However, stereospecific syntheses of (R)-5-((E)-2-pyrrolidin-3-ylvinyl)pyrimidine, which are scalable to a large-scale production, are desirable. Furthermore, because (R)-5-((E)-2-pyrrolidin-3-ylvinyl)pyrimidine in the free base form is a viscous oil with limited water solubility and stability, there is a need for salt forms that display improved properties, including purity, stability, solubility, and bioavailability. Preferential characteristics of these novel salt forms include those that would increase the ease or efficiency of manufacture of the active ingredient and its formulation into a commercial product. Lastly, there is a need for stable polymorphic forms of these salts that allows for an increase the ease or efficiency of manufacture of the active ingredient and its formulation into a commercially product.

SUMMARY OF THE INVENTION

One aspect of the present invention is an acid addition salt of (R)-5-((E)-2-pyrrolidin-3-ylvinyl)pyrimidine. In certain embodiments, the acid is selected from hydrochloric, sulfuric, methanesulfonic, maleic, phosphoric, 1-hydroxy-2-naphthoic, ketoglutaric, malonic, L-tartaric, fumaric, citric, L-malic, hippuric, L-lactic, benzoic, succinic, adipic, acetic, nicotinic, propionic, orotic, 4-hydroxybenzoic, di-p-toluoyl-D-tartaric, di-p-anisoyl-D-tartaric, di-benzoyl-D-tartaric, 10-camphorsulfonic, camphoric, or phencyphos.

One aspect of the invention is a maleic acid salt of (R)-5-((E)-2-pyrrolidin-3-ylvinyl)pyrimidine. Another aspect of the invention is an orotic acid salt of (R)-5-((E)-2-pyrrolidin-3-ylvinyl)pyrimidine. A further aspect of the invention is a citric acid salt of (R)-5-((E)-2-pyrrolidin-3-ylvinyl)pyrimidine.

One aspect of the invention is a (R)-5-((E)-2-pyrrolidin-3-ylvinyl)pyrimidine mono-citrate. Another aspect of the invention is a crystalline polymorph of (R)-5-((E)-2-pyrrolidin-3-ylvinyl)pyrimidine mono-citrate.

On aspect of the invention is a stereospecific synthesis of (R)-5-((E)-2-pyrrolidin-3-ylvinyl)pyrimidine. Other aspects and embodiments of the present invention will be described herein. The scope of the present invention includes combinations of aspects, embodiments, and preferences.

DETAILED DESCRIPTION

Definitions

Figure 1:
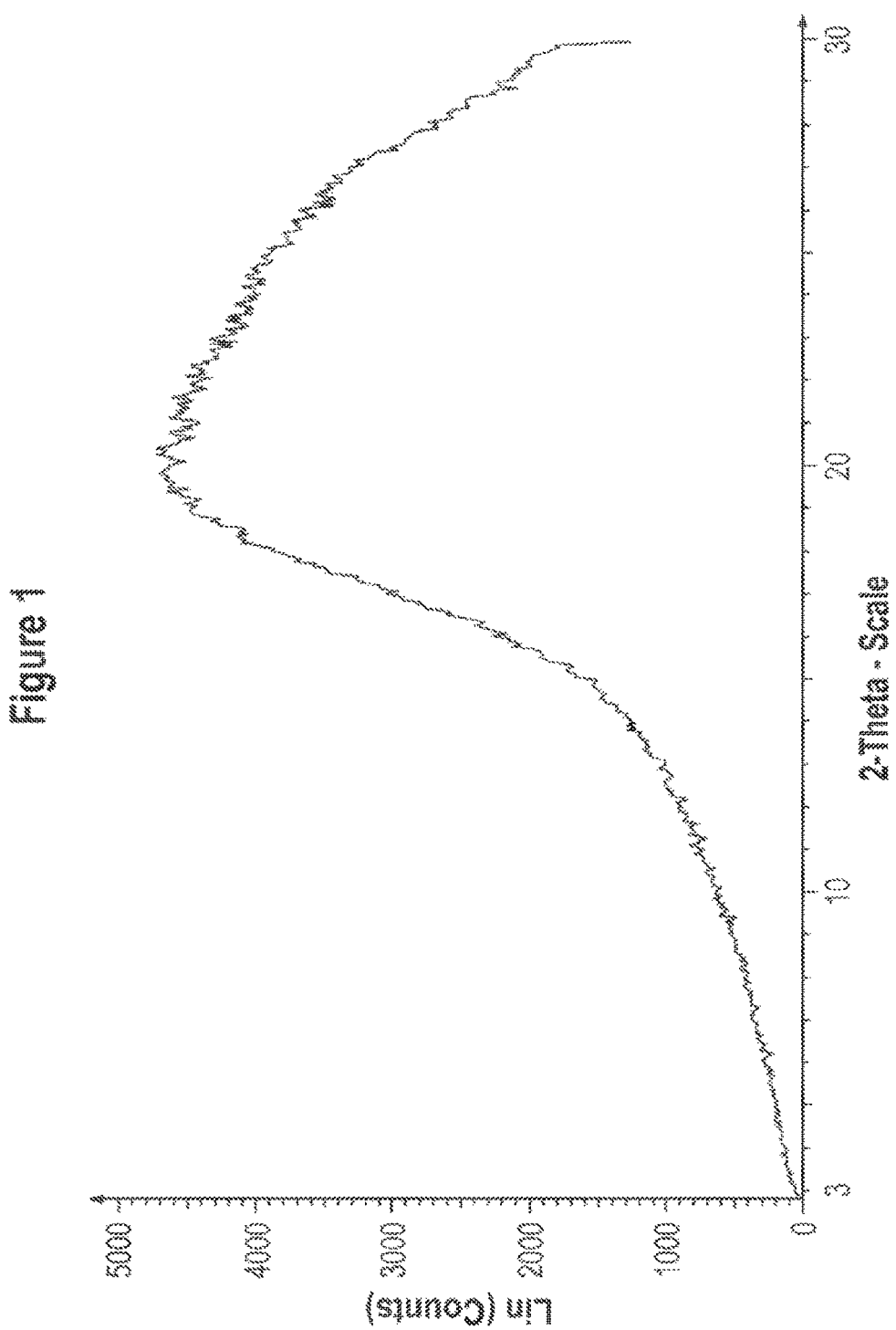
FIG. 1 is an XRPD pattern of amorphous form of (R)-5-((E)-2-pyrrolidin-3-ylvinyl)pyrimidine mono-citrate.

The following definitions are meant to clarify, but not limit, the terms defined. If a particular term used herein is not specifically defined, such term should not be considered indefinite. Rather, terms are used within their accepted meanings.

The phrase "compounds of the present invention" as used herein refers to (R)-5-((E)-2-pyrrolidin-3-ylvinyl)pyrimidine or an acid addition salt thereof. The acid is selected from hydrochloric acid, sulfuric acid, methanesulfonic acid, maleic acid, phosphoric acid, 1-hydroxy-2-naphthoic acid, ketoglutaric acid, malonic acid, L-tartaric acid, fumaric acid, citric acid, L-malic acid, hippuric acid, L-lactic acid, benzoic acid, succinic acid, adipic acid, acetic acid, nicotinic acid, propionic acid, orotic acid, 4-hydroxybenzoic acid, di-p-toluoyl-D-tartaric acid, di-p-anisoyl-D-tartaric acid, di-benzoyl-D-tartaric acid, 10-camphorsulfonic acid, camphoric acid, or 2-hydroxy-5,5-dimethyl-4-phenyl-1,3,2-dioxaphosphorinan-2-one (phencyphos). The phrase includes a hydrate or a solvate form.

Further, as used herein, the term "compound" may be used to mean the free base form, or alternatively, a salt form of (R)-5-((E)-2-pyrrolidin-3-ylvinyl)pyrimidine, depending on the context, which will be readily apparent. Those skilled in the art will be able to distinguish the difference.

As used herein, the term "pharmaceutically acceptable" refers to carrier(s), diluent(s), excipient(s) or salt forms that are compatible with the other ingredients of the formulation and not deleterious to the recipient of the pharmaceutical composition.

As used herein, the term "pharmaceutical composition" refers to a compound of the present invention optionally admixed with one or more pharmaceutically acceptable carriers, diluents, excipients, or adjuvants. Pharmaceutical compositions preferably exhibit a degree of stability to environmental conditions so as to make them suitable for manufacturing and commercialization purposes.

As used herein, the terms "effective amount," "therapeutic amount," or "effective dose" refer to an amount of active ingredient sufficient to elicit the desired pharmacological or therapeutic effects, thus resulting in effective prevention or treatment of a disorder. Prevention of a disorder may be manifested by delaying or preventing the progression of the disorder, as well as delaying or preventing the onset of the symptoms associated with the disorder. Treatment of the disorder may be manifested by a decrease or elimination of symptoms, inhibition or reversal of the progression of the disorder, as well as any other contribution to the well being of the patient.

The effective dose can vary, depending upon factors such as the condition of the patient, the severity of the symptoms of the disorder, and the manner in which the pharmaceutical composition is administered. Typically, to be administered in an effective dose, compounds are required to be administered in an amount of less than 5 mg/kg of patient weight. Often, the compounds may be administered in an amount from less than about 1 mg/kg patient weight to less than about 100 µg/kg of patient weight, and occasionally between about 10 µg/kg to less than 100 µg/kg of patient weight. The foregoing effective doses typically represent that amount administered as a single dose, or as one or more doses administered over a 24 hours period. For human patients, the effective dose of the compounds may require administering the compound in an amount of at least about 1 mg/24 hr/patient, but not more than about 1000 mg/24 hr/patient, and often not more than about 500 mg/24 hr/patient.

As used herein, the phrase "substantially crystalline" includes greater than 20%, preferably greater than 30%, and more preferably greater than 40% (e.g. greater than any of 50, 60, 70, 80, or 90%) crystalline.

The term "stability" as defined herein includes chemical stability and solid state stability, where the phrase "chemical stability" includes the potential to store salts of the invention in an isolated form, or in the form of a formulation in which it is provided in admixture with pharmaceutically acceptable carriers, diluents, excipients, or adjuvants, such as in an oral dosage form, such as a tablet, capsule, or the like, under normal storage conditions, with an insignificant degree of chemical degradation or decomposition, and the phrase "solid state stability", includes the potential to store salts of the invention in an isolated solid form, or in the form of a solid formulation in which it is provided in admixture with pharmaceutically acceptable carriers, diluents, excipients, or adjuvants, such as in an oral dosage form, such as a tablet, capsule, or the like, under normal storage conditions, with an insignificant degree of solid state transformation, such as crystallization, recrystallization, solid state phase transition, hydration, dehydration, solvation, or desolvation.

Examples of "normal storage conditions" include one or more of temperatures of between −80° C. and 50° C., preferably between 0° C. and 40° C. and more preferably ambient temperatures, such as 15° C. to 30° C., pressures of between 0.1 and 2 bars, preferably at atmospheric pressure, relative humidity of between 5 and 95%, preferably 10 to 60%, and exposure to 460 lux or less of UV/visible light, for prolonged periods, such as greater than or equal to six months. Under such conditions, salts of the invention may be found to be less than 5%, more preferably less than 2%, and especially less than 1%, chemically degraded or decomposed, or solid state transformed, as appropriate. The skilled person will appreciate that the above-mentioned upper and lower limits for temperature, pressure, and relative humidity represent extremes of normal storage conditions, and that certain combinations of these extremes will not be experienced during normal storage (e.g. a temperature of 50° C. and a pressure of 0.1 bar).

Compounds

One embodiment of the present invention includes (R)-5-((E)-2-pyrrolidin-3-ylvinyl)pyrimidine (Formula I) or a pharmaceutically acceptable salt thereof.

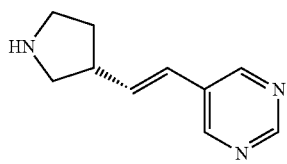

Formula I

In one embodiment, the compound of Formula I or a pharmaceutically acceptable salt thereof is substantially pure. In one embodiment, the compound of Formula I or a pharmaceutically acceptable salt thereof is substantially free of (S)-5-((E)-2-pyrrolidin-3-ylvinyl)pyrimidine. In one embodiment, the compound of Formula I or a pharmaceutically acceptable salt thereof is present in an amount of about 75% by weight compared to (S)-5-((E)-2-pyrrolidin-3-ylvinyl)pyrimidine, preferably greater than 85% by weight, more preferably greater than 95% by weight, more preferably greater than 98% by weight, and most preferably 99% by weight or greater.

One embodiment of the present invention includes a method for the preparation of (R)-5-((E)-2-pyrrolidin-3-ylvinyl)pyrimidine or a pharmaceutically acceptable salt thereof containing less than 25%, preferably less than 15%, more preferably less than 5%, even more preferably less than 2%, and most preferably less than 1% of (S)-5-((E)-2-pyrrolidin-3-ylvinyl)pyrimidine by weight. Another embodiment of the present invention includes a method for the preparation of (R)-5-((E)-2-pyrrolidin-3-ylvinyl)pyrimidine or a pharmaceutically acceptable salt thereof containing less than 25%, preferably less than 15%, more preferable less than 5%, even more preferably less than 2%, and most preferably less than 1% of (S)-5-((E)-2-pyrrolidin-3-ylvinyl) pyrimidine by weight, without the use of a chiral chromatographic separation step.

One embodiment of the present invention includes a method for the preparation of (R)-5-((E)-2-pyrrolidin-3-ylvinyl)pyrimidine or a pharmaceutically acceptable salt thereof containing less than 25%, preferably less than 15%, more preferably less than 5%, even more preferably less than 2%, and most preferably less than 1% of (S)-5-((E)-2-pyrrolidin-3-ylvinyl)pyrimidine by weight. Another embodiment of the present invention includes a method for the preparation of (R)-5-((E)-2-pyrrolidin-3-ylvinyl)pyrimidine or a pharmaceutically acceptable salt thereof containing less than 25%, preferably less than 15%, more preferable less than 5%, even more preferably less than 2%, and most preferably less than 1% of (S)-5-((E)-2-pyrrolidin-3-ylvinyl) pyrimidine by weight, without the use of a chiral chromatographic separation step. Thus, in one embodiment of the present invention, a method for the manufacture of substantially pure (R)-5-((E)-2-pyrrolidin-3-ylvinyl)pyrimidine is provided, without reliance upon chromatographic separation. One embodiment of the present invention includes a method of manufacturing a compound of the present invention on a commercial scale, namely where the method is fully validated cGMP commercial scale active pharmaceutical ingredient (API) manufacturing, with reference to 21 CFR Parts 210 and 211, herein incorporated by reference.

One embodiment of the present invention includes use of (R)-5-((E)-2-pyrrolidin-3-ylvinyl)pyrimidine or a pharmaceutically acceptable salt thereof in the manufacture of a medicament.

One embodiment of the present invention includes a method for the treatment or prevention of a variety of disorders and dysfunctions, comprising administering to a mammal in need of such treatment, a therapeutically effective amount of (R)-5-((E)-2-pyrrolidin-3-ylvinyl)pyrimidine or a pharmaceutically acceptable salt thereof. More specifically, the disorder or dysfunction may be selected from the group consisting of CNS disorders, inflammation, inflammatory response associated with bacterial and/or viral infection, pain, metabolic syndrome, autoimmune disorders or other disorders described in further detail herein. Another embodiment of the present invention includes compounds that have utility as diagnostic agents and in receptor binding studies as described herein.

One embodiment of the present invention includes a pharmaceutical composition comprising a therapeutically effective amount of (R)-5-((E)-2-pyrrolidin-3-ylvinyl)pyrimidine or a pharmaceutically acceptable salt thereof and one or more pharmaceutically acceptable carrier. One embodiment of the present invention includes the use of a pharmaceutical composition of the present invention in the manufacture of a medicament for treatment of central nervous system disorders and dysfunctions. Another embodiment of the present invention includes (R)-5-((E)-2-pyrrolidin-3-ylvinyl)pyrimidine or a pharmaceutically acceptable salt thereof with reference to any one of the Examples. Another embodiment of the present invention (R)-5-((E)-2-pyrrolidin-3-ylvinyl)pyrimidine or a pharmaceutically acceptable salt thereof for use as an active therapeutic substance. Another embodiment of the present invention includes (R)-5-((E)-2-pyrrolidin-3-ylvinyl)pyrimidine or a pharmaceutically acceptable salt thereof for use to modulate an NNR in a subject in need thereof. Another embodiment of the present invention includes (R)-5-((E)-2-pyrrolidin-3-ylvinyl)pyrimidine or a pharmaceutically acceptable salt thereof for use in the treatment or prevention of conditions or disorders mediated by NNR. Another embodiment of the present invention includes a use (R)-5-((E)-2-pyrrolidin-3-ylvinyl)pyrimidine or a pharmaceutically acceptable salt thereof in the manufacture of a medicament for use of modulating NNR in a subject in need thereof. Another embodiment of the present invention includes a use of (R)-5-((E)-2-pyrrolidin-3-ylvinyl)pyrimidine or a pharmaceutically acceptable salt thereof in the manufacture of a medicament for use in the treatment or prevention of conditions or disorders mediated by NNR. Another embodiment of the present invention includes a method of modulating NNR in a subject in need thereof through the administration of (R)-5-((E)-2-pyrrolidin-3-ylvinyl)pyrimidine or a pharmaceutically acceptable salt thereof.

Unless otherwise stated, structures depicted herein are also meant to include compounds which differ only in the presence of one or more isotopically enriched atoms. For example, compounds having the present structure except for the replacement of a hydrogen atom by deuterium or tritium, or the replacement of a carbon atom by $^{13}C$ or $^{14}C$, or the replacement of a nitrogen atom by $^{15}N$, or the replacement of an oxygen atom with $^{17}O$ or $^{18}O$ are within the scope of the invention. Such isotopically labeled compounds are useful as research or diagnostic tools.

As noted herein, the present invention includes specific representative compounds, which are identified herein with particularity. The compounds of this invention may be made by a variety of methods, including well-known standard synthetic methods. Illustrative general synthetic methods are set out below and then specific compounds of the invention are prepared in the working Examples.

In all of the examples described below, protecting groups for sensitive or reactive groups are employed where necessary in accordance with general principles of synthetic chemistry. Protecting groups are manipulated according to standard methods of organic synthesis (T. W. Green and P. G. M. Wuts, *Protecting Groups in Organic Synthesis*, 3$^{rd}$ Edition, John Wiley & Sons, New York (1999)). These groups are removed at a convenient stage of the compound synthesis using methods that are readily apparent to those skilled in the art. The selection of processes as well as the reaction conditions and order of their execution shall be consistent with the preparation of compounds of the present invention.

The present invention also provides a method for the synthesis of compounds useful as intermediates.

General Synthetic Methods

One aspect of the present invention includes the method for the stereospecific synthesis of (R)-5-((E)-2-pyrrolidin-3-ylvinyl)pyrimidine (11) outlined in Scheme 1. Commercially available tert-butyl (R)-3-hydroxypyrrolidine-1-carboxylate (compound 1) is treated with methanesulfonyl chloride to give tert-butyl (R)-3-(methylsulfonyloxy)pyrrolidine-1-carboxylate (compound 2), which then is reacted with diethylmalonate and a suitable base (e.g., potassium tert-butoxide or sodium ethoxide) to give diethyl (R)-2-(1-(tert-butoxycarbonyl)pyrrolidin-3-yl)malonate (compound 3) with inverted stereochemistry around the chiral carbon.

Suitable solvents for these reactions may be selected from the group of toluene, xylenes, 1-methyl-2-pyrrolidinone, dimethylformamide, dimethylacetamide, ethanol, tert-butanol, tetrahydrofuran, 1,2-dimethoxyethane, dioxane, and mixtures thereof. In one embodiment the solvent for the methanesulfonic ester formation toluene, and the solvent for the malonate displacement is 1-methyl-2-pyrrolidinone. In another embodiment the solvent for the malonate displacement is ethanol. Suitable bases for these reactions may be selected from the group of triethylamine, diethylisopropylamine, diisopropylethylamine, potassium tert-butoxide, sodium metal, sodium hydride, sodium ethoxide, potassium hydride and lithium hydride. In one embodiment the base for the methanesulfonic ester formation is triethylamine, and the base for the malonate displacement is potassium tert-butoxide. In another embodiment the base for the malonate displacement is sodium ethoxide.

Hydrolysis of diester 3 with aqueous potassium hydroxide yields (R)-2-(1-(tert-butoxycarbonyl)pyrrolidin-3-yl)malonic acid (compound 4), which is decarboxylated to afford (R)-2-(1-(tert-butoxycarbonyl)pyrrolidin-3-yl)acetic acid (compound 5). Suitable solvents for these reactions may be selected from the group of water, ethanol, tetrahydrofuran, dimethylformamide, dimethylacetamide, 1,2-dimethoxyethane, dioxane, 1-methyl-2-pyrrolidinone, toluene, dimethylsulfoxide, and mixtures thereof. In one embodiment the solvent for the ester hydrolysis is aqueous tetrahydrofuran, and the solvent for the decarboxylation is 1-methyl-2-pyrrolidinone. In another embodiment the solvent for the ester hydrolysis is ethanol, and the solvent for the decarboxylation is a mixture of dimethylsulfoxide and toluene. Suitable bases for the hydrolysis reaction may be selected from the group of potassium hydroxide, sodium hydroxide, potassium carbonate, sodium carbonate, barium hydroxide and cesium carbonate. In one embodiment the base is potassium hydroxide. Reduction of compound 5 gives tert-butyl (R)-3-(2-hydroxyethyl)pyrrolidine-1-carboxylate (compound 6), which may be reacted with methanesulfonyl chloride and then sodium iodide to give tert-butyl (R)-3-(2-(methylsulfonyloxy)ethyl)pyrrolidine-1-carboxylate (compound 7) and tert-butyl (R)-3-(2-iodoethyl)pyrrolidine-1-carboxylate (compound 8), respectively. Suitable solvents for the reduction reaction may be selected from the group of tetrahydrofuran, ether, dioxane, 1,2-dimethoxyethane, and mixtures thereof. In one embodiment the solvent is tetrahydrofuran. Suitable reducing agents may be selected from the group of borane, diborane, borane-tetrahydrofuran complex, borane-dimethyl ether complex and borane-dimethylsulfide complex. Suitable solvents for the methanesulfonic ester formation may be selected from the group of toluene, xylenes, ether, tetrahydrofuran, 1,2-dimethoxyethane, dioxane, and mixtures thereof. In one embodiment the solvent for the methanesulfonic ester formation is toluene. Suitable bases for the methanesulfonic ester formation may be selected from the group of triethylamine, diethylisopropylamine and diisopropylethylamine. In one embodiment the base for the methanesulfonic ester formation is triethylamine. Suitable solvents for the iodide displacement may be selected from the group of 1-methyl-2-pyrrolidinone, dimethylformamide, dimethylacetamide, ethanol, tert-butanol, tetrahydrofuran, 1,2-dimethoxyethane, dioxane, dimethylsulfoxide, and mixtures thereof. In one embodiment the solvent for the iodide displacement is 1,2-dimethoxyethane.

Finally, treatment of compound 8 with potassium tert-butoxide gives of compound 9. Suitable solvents for this reaction may be selected from the group of 1,2-dimethoxyethane, 1-methyl-2-pyrrolidinone, dimethylformamide, dimethylacetamide, ethanol, tetrahydrofuran, dioxane and mixtures thereof. In one embodiment the solvent is 1,2-dimethoxyethane. Suitable bases for this reaction may be selected from the group of potassium tert-butoxide, sodium ethoxide and diazabicycloundecane. In another embodiment the base is potassium tert-butoxide.

Palladium-catalyzed coupling of compound 9 with 5-bromopyrimidine yields (R)-1-(tert-butoxycarbonyl)-5-((E)-2-pyrrolidin-3-ylvinyl)pyrimidine (10), which is de-protected in the final step to give (R)-5-((E)-2-pyrrolidin-3-ylvinyl)pyrimidine (11). Suitable solvents for the palladium-catalyzed coupling reaction may be selected from the group of 1-methyl-2-pyrrolidinone, dimethylformamide, dimethylacetamide and acetonitrile. In one embodiment the solvent is dimethylacetamide. Suitable bases for the palladium catalyzed coupling reaction may be selected from the group of triethylamine, diethylisopropylamine, diisopropylethylamine, and sodium acetate. In one embodiment the base is sodium acetate. Suitable phosphine ligands for the palladium catalyzed coupling reaction may be selected from the group of tri-n-butylphosphine, tri-tert-butylphosphine, tricyclohexylphosphine, triphenylphosphine, tri-o-tolylphosphine and 1,1'-bis(diphenylphosphino)ferrocene. In one embodiment the phosphine ligand is 1,1'-bis(diphenylphosphino)ferrocene. Suitable palladium catalysts for the palladium catalyzed coupling reaction may be selected from the group of palladium acetate, palladium chloride and dipalladium tris(dibenzylacetone). In one embodiment the palladium catalyst is palladium acetate. Suitable solvents for the de-protection reaction may be selected from the group of water, dichloromethane, chloroform and dichloroethane. In one embodiment the solvent is water. Suitable acids for the de-protection reaction may be selected from the group of trifluoroacetic acid, hydrochloric acid and sulfuric acid. In one embodiment the acid is hydrochloric acid.

Those skilled in the art of organic synthesis will appreciate that there exist multiple means of producing compounds of the present invention which are labeled with a radioisotope appropriate to various diagnostic uses. For example, coupling of $^{11}$C-labeled 5-bromopyrimidine with compound 9 or followed by removal of the protecting group as described will produce a compound suitable for use in positron emission tomography.

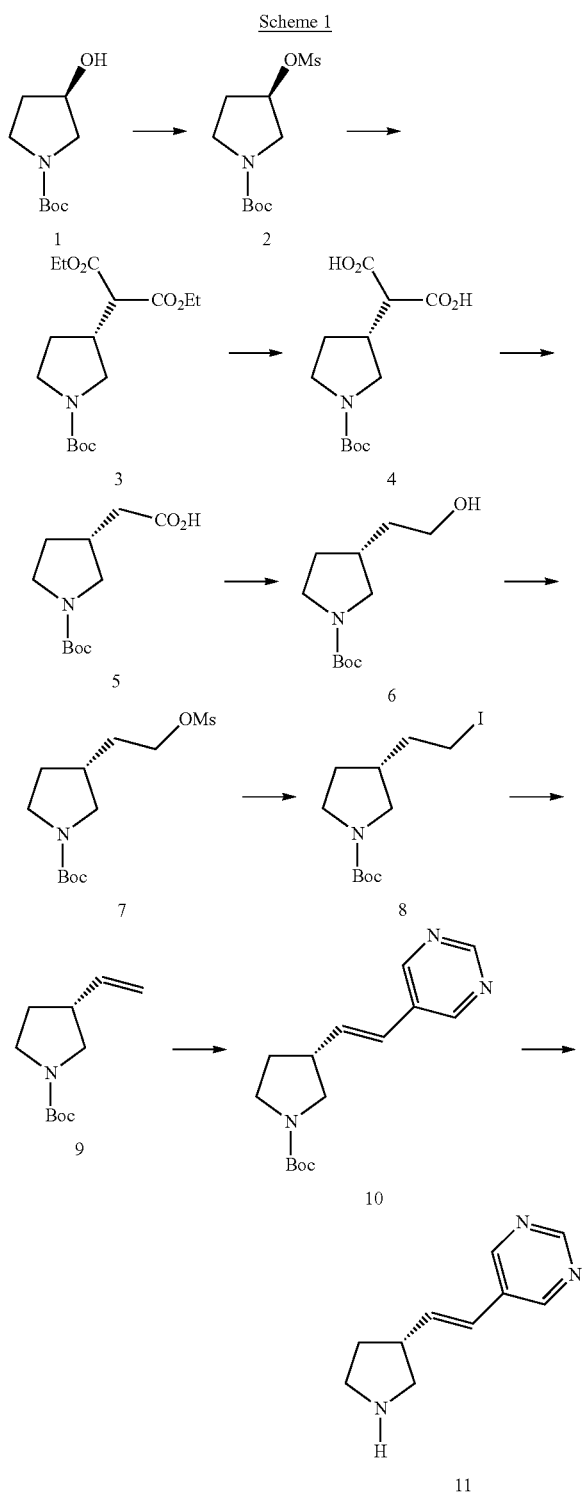

Scheme 1

Salt Forms

One aspect of the present invention relates to novel salt forms of (R)-5-((E)-2-pyrrolidin-3-ylvinyl)pyrimidine. (R)-5-((E)-2-Pyrrolidin-3-ylvinyl)pyrimidine in the free base form is a viscous oil with limited water solubility. However, the free base will react with both inorganic and organic acids to make certain acid addition salts that have physical properties that are advantageous for the preparation of pharmaceutical compositions such as crystallinity, water solubility, and stability toward chemical degradation. Typically these salt forms are pharmaceutically acceptable salts.

One aspect of the present invention includes acid addition salts of (R)-5-((E)-2-pyrrolidin-3-ylvinyl)pyrimidine. The acid is selected from hydrochloric acid, sulfuric acid, methanesulfonic acid, maleic acid, phosphoric acid, 1-hydroxy-2-naphthoic acid, ketoglutaric acid, malonic acid, L-tartaric acid, fumaric acid, citric acid, L-malic acid, hippuric acid, L-lactic acid, benzoic acid, succinic acid, adipic acid, acetic acid, nicotinic acid, propionic acid, orotic acid, 4-hydroxybenzoic acid, di-p-toluoyl-D-tartaric acid, di-p-anisoyl-D-tartaric acid, di-benzoyl-D-tartaric acid, 10-camphorsulfonic acid, camphoric acid, and phencyphos. The present invention also includes hydrates and solvates of these salt forms.

The stoichiometry of the salts comprising the present invention can vary. For example, it is typical that the molar ratio of acid to (R)-5-((E)-2-pyrrolidin-3-ylvinyl)pyrimidine is 1:2 or 1:1, but other ratios, such as 3:1, 1:3, 2:3, 3:2 and 2:1, are possible. Depending upon the manner by which the salts described herein are formed, the salts can have crystal structures that occlude solvents that are present during salt formation. Thus, the salts can occur as hydrates and other solvates of varying stoichiometry of solvent relative to (R)-5-((E)-2-pyrrolidin-3-ylvinyl)pyrimidine.

In one embodiment of the present invention, the salt has a stoichiometry of acid to (R)-5-((E)-2-pyrrolidin-3-ylvinyl)pyrimidine of 1:2. In another embodiment, the salt has a stoichiometry of acid to (R)-5-((E)-2-pyrrolidin-3-ylvinyl)pyrimidine of 1:1.

Another embodiment of the present invention includes (R)-5-((E)-2-pyrrolidin-3-ylvinyl)pyrimidine mono-citrate or a hydrate or solvate thereof. Another embodiment of the present invention includes (R)-5-((E)-2-pyrrolidin-3-ylvinyl)pyrimidine mono-orotate or a hydrate or solvate thereof. Another embodiment of the present invention includes (R)-5-((E)-2-pyrrolidin-3-ylvinyl)pyrimidine mono-maleate or a hydrate or solvate thereof.

A further aspect of the present invention comprises processes for the preparation of the salts. The precise conditions under which the salts are formed may be empirically determined. The salts may be obtained by crystallization under controlled conditions.

The method for preparing the salt forms can vary. The preparation of (R)-5-((E)-2-pyrrolidin-3-ylvinyl)pyrimidine salt forms typically involves:

(i) mixing the free base, or a solution of the free base of suitably pure (R)-5-((E)-2-pyrrolidin-3-ylvinyl)pyrimidine in a suitable solvent, with any of the acids in pure form or as a solution of any of the acids in a suitable solvent, typically 0.5 to 1 equivalents of the acid, (ii) (a) cooling the resulting salt solution if necessary to cause precipitation, or (ii) (b) adding a suitable anti-solvent to cause precipitation, or (ii) (c) evaporating the first solvent and adding a new solvent and repeating either steps (ii) (a) or step (ii) (b), and (iii) filtering to collect the salt, and optional recrystallization.

The stoichiometry, solvent mix, solute concentration, and temperature employed can vary. Representative solvents that can be used to prepare or recrystallize the salt forms include, without limitation, ethanol, methanol, isopropyl alcohol, isopropyl acetate, acetone, ethyl acetate, toluene, water, methyl ethyl ketone, methyl isobutyl ketone, tert-butyl methyl ether, tetrahydrofuran, dichloromethane, n-heptane, and acetonitrile.

One embodiment of the present invention comprises the hydrochloric acid, sulfuric acid, methanesulfonic acid, maleic acid, phosphoric acid, 1-hydroxy-2-naphthoic acid, ketoglutaric acid, malonic acid, L-tartaric acid, fumaric acid, citric acid, L-malic acid, hippuric acid, L-lactic acid, benzoic acid, succinic acid, adipic acid, acetic acid, nicotinic acid, propionic acid, orotic acid, 4-hydroxybenzoic acid, di-p-toluoyl-D-tartaric acid, di-p-anisoyl-D-tartaric acid, dibenzoyl-D-tartaric acid, 10-camphorsulfonic acid, camphoric acid, and phencyphos salts of (R)-5-((E)-2-pyrrolidin-3-ylvinyl)pyrimidine in substantially crystalline form.

The degree (%) of crystallinity may be determined by the skilled person using x-ray powder diffraction (XRPD). Other techniques, such as solid state NMR, FT-IR, Raman spectroscopy, differential scanning calorimetry (DSC) and microcalorimetry, may also be used. For compounds of the current invention, it has been found to be possible to produce salts in forms which are greater than 80% crystalline.

Several of these crystalline salts demonstrated stability sufficient to establish their promise in the production of pharmaceutical preparations. Such stability can be demonstrated in a variety of ways. Propensity to gain and release atmospheric moisture can be assessed by dynamic vapor sorption (DVS). Stability to elevated temperatures and humidity can be studied by storing the solid salts at 40° C./75% RH for up to eight days, and then re-examining each by weight, appearance under the microscope, and XRPD.

Polymorphs

The compounds of the present invention may crystallize in more than one form, a characteristic known as polymorphism, and such polymorphic forms ("polymorphs") are within the scope of the present invention. Polymorphism generally can occur as a response to changes in temperature, pressure, or both. Polymorphism can also result from variations in the crystallization process. Polymorphs can be distinguished by various physical characteristics known in the art such as XRPD patterns (diffractograms), solubility in various solvents, and melting point.

The present invention includes various polymorphic forms of the salt forms of (R)-5-((E)-2-pyrrolidin-3-ylvinyl) pyrimidine, including hydrates and solvates of the salts. Such polymorphic forms are characterized by their x-ray powder diffraction (XRPD) patterns (diffractograms).

One embodiment of the present invention includes a crystalline form of (R)-5-((E)-2-pyrrolidin-3-ylvinyl)pyrimidine mono-citrate. Another embodiment of the present invention includes an amorphous form of (R)-5-((E)-2-pyrrolidin-3-ylvinyl)pyrimidine mono-citrate. Another embodiment of the present invention includes an amorphous form of (R)-5-((E)-2-pyrrolidin-3-ylvinyl)pyrimidine mono-citrate whose XRPD pattern substantially corresponds to that shown in FIG. 1.

One embodiment of the present invention includes a polymorphic form of (R)-5-((E)-2-pyrrolidin-3-ylvinyl)pyrimidine mono-citrate Form I characterized by a XRPD pattern comprising at least one of the following peaks:

| 2θ |
|---|
| 5.27 |
| 10.03 |
| 13.77 |
| 21.73 |

Figure 2:
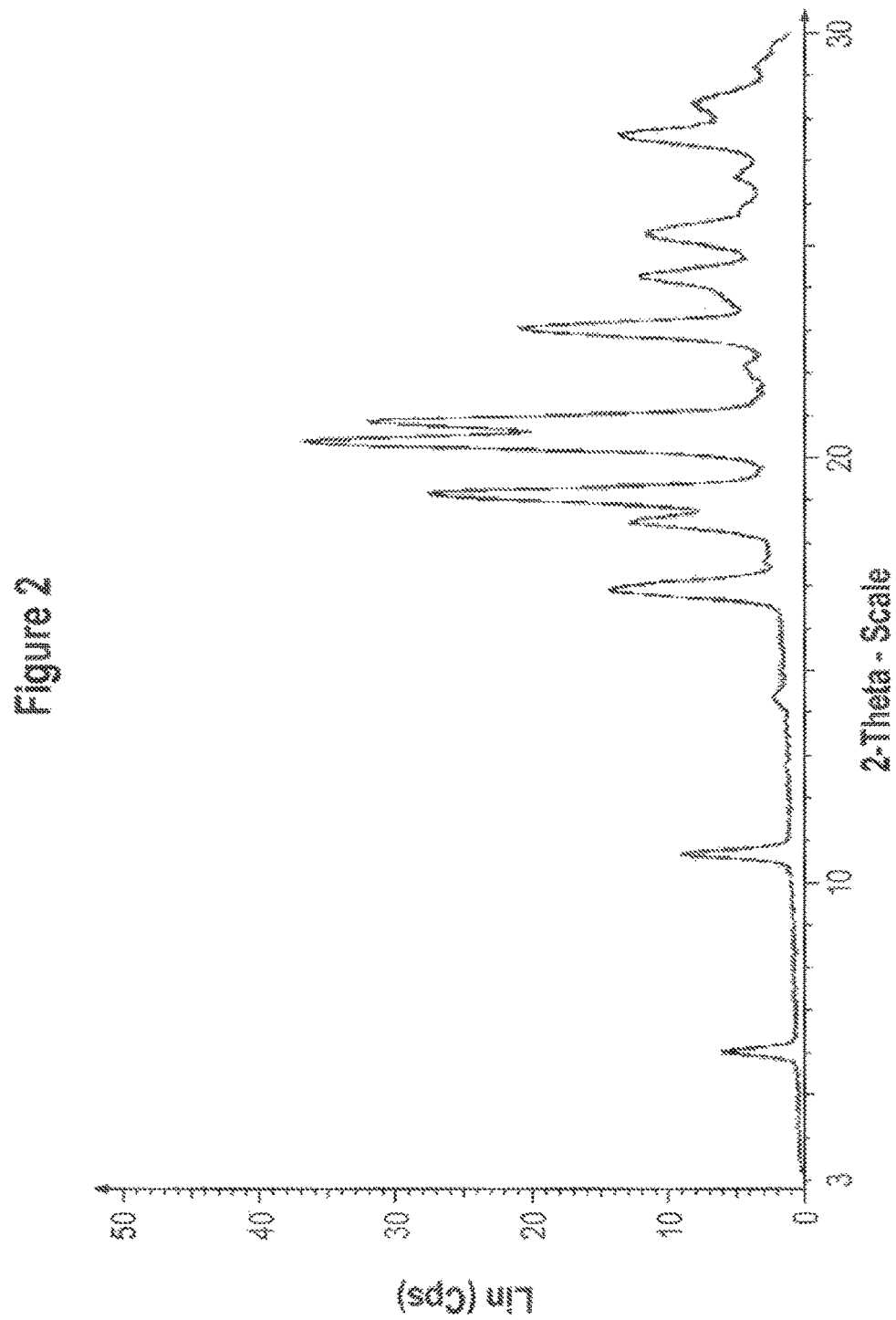
FIG. 2 is an XRPD pattern of Form I (R)-5-((E)-2-pyrrolidin-3-ylvinyl)pyrimidine mono-citrate.

Another embodiment, the present invention includes a polymorphic form of (R)-5-((E)-2-pyrrolidin-3-ylvinyl)pyrimidine mono-citrate Form I whose XRPD pattern substantially corresponds to that shown in FIG. 2.

One embodiment of the present invention includes a polymorphic form of (R)-5-((E)-2-pyrrolidin-3-ylvinyl)pyrimidine mono-citrate Form II characterized by a powder x-ray diffraction pattern comprising at least one of the following peaks:

| 2θ |
|---|
| 11.02 |
| 20.01 |
| 22.06 |
| 24.66 |
| 32.13 |
| 33.35 |
| 34.61 |
| 35.96 |
| 38.65 |
| 40.23 |

Figure 3:
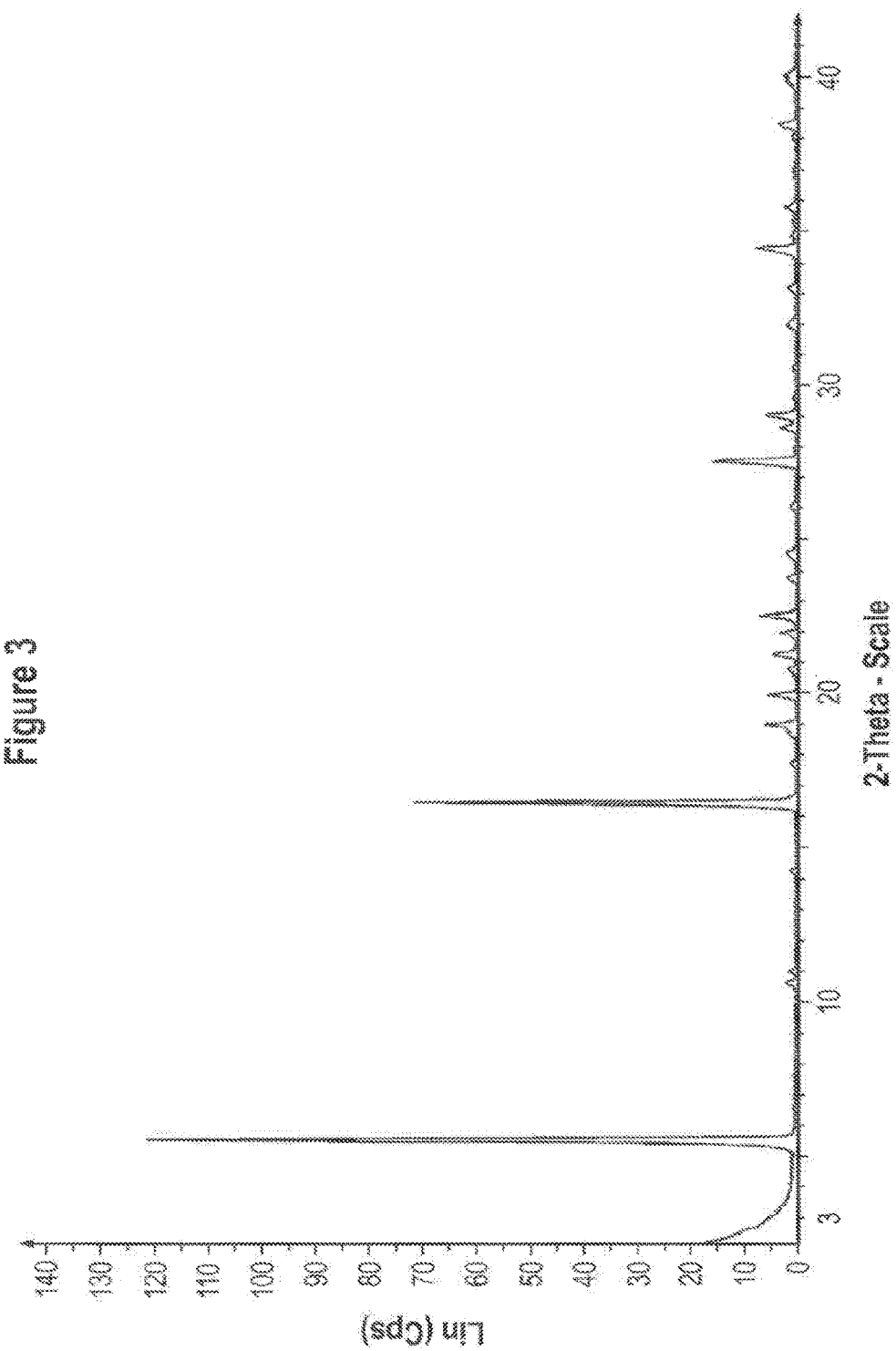
FIG. 3 is an XRPD pattern of Form II (R)-5-((E)-2-pyrrolidin-3-ylvinyl)pyrimidine mono-citrate.

Another embodiment, the present invention includes a polymorphic form of (R)-5-((E)-2-pyrrolidin-3-ylvinyl)pyrimidine mono-citrate Form II whose XRPD pattern substantially corresponds to that shown in FIG. 3.

One embodiment of the present invention includes a polymorphic form of (R)-5-((E)-2-pyrrolidin-3-ylvinyl)pyrimidine mono-citrate Form III characterized by a XRPD pattern comprising at least one of the following peaks:

| 2θ |
|---|
| 9.43 |
| 12.24 |
| 16.24 |
| 18.38 |
| 19.18 |
| 19.48 |
| 21.52 |
| 22.89 |
| 23.08 |
| 24.28 |
| 30.77 |
| 31.27 |
| 32.36 |
| 33.09 |
| 34.86 |
| 37.26 |
| 37.63 |
| 39.47 |

Figure 4:
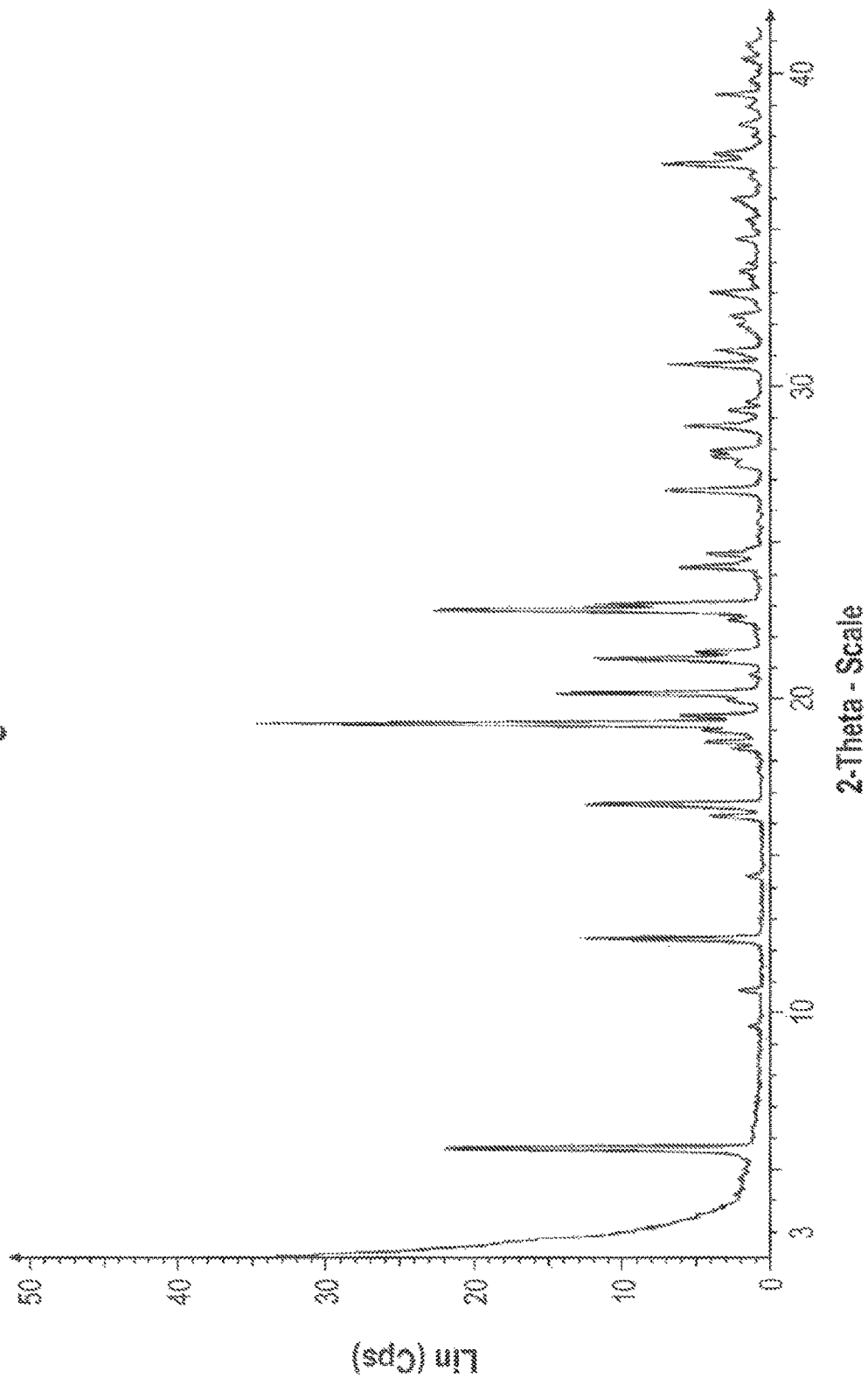
FIG. 4 is an XRPD pattern of Form III (R)-5-((E)-2-pyrrolidin-3-ylvinyl)pyrimidine mono-citrate.

Another embodiment, the present invention includes a polymorphic form of (R)-5-((E)-2-pyrrolidin-3-ylvinyl)pyrimidine mono-citrate Form III whose XRPD pattern substantially corresponds to that shown in FIG. 4.

One embodiment of the present invention includes a polymorphic form of (R)-5-((E)-2-pyrrolidin-3-ylvinyl)pyrimidine mono-citrate Form IV characterized by a XRPD pattern comprising at least one of the following peaks:

| 2θ |
|---|
| 5.05 |
| 10.81 |
| 14.06 |
| 15.20 |
| 17.43 |
| 23.57 |
| 24.21 |
| 25.52 |
| 26.95 |

Figure 5:
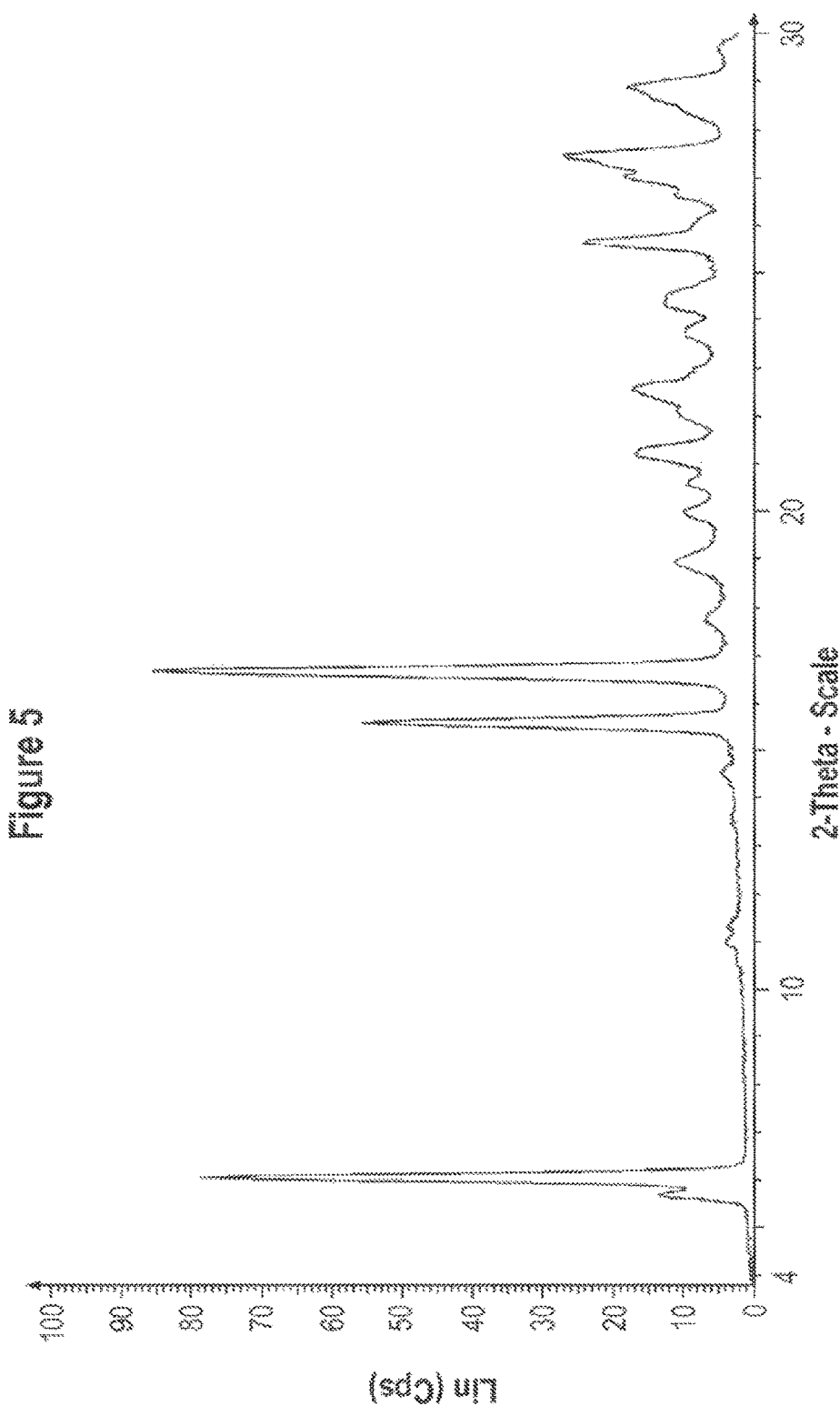
FIG. 5 is an XRPD pattern of Form IV (R)-5-((E)-2-pyrrolidin-3-ylvinyl)pyrimidine mono-citrate.

Another embodiment, the present invention includes a polymorphic form of (R)-5-((E)-2-pyrrolidin-3-ylvinyl)pyrimidine mono-citrate Form IV whose XRPD pattern substantially corresponds to that shown in FIG. 5

One embodiment of the present invention includes a crystalline form of (R)-5-((E)-2-pyrrolidin-3-ylvinyl)pyrimidine mono-orotate.

One embodiment of the present invention includes a polymorphic form of (R)-5-((E)-2-pyrrolidin-3-ylvinyl)pyrimidine mono-orotate Form I characterized by a XRPD pattern comprising at least one of the following peaks:

| 2θ |
|---|
| 2.55 |
| 6.54 |
| 8.66 |
| 13.26 |
| 14.56 |
| 15.98 |
| 17.47 |
| 18.53 |
| 19.30 |
| 20.26 |
| 21.05 |
| 22.02 |
| 23.14 |
| 24.32 |
| 25.56 |
| 26.87 |
| 27.84 |
| 28.76 |
| 29.53 |

Figure 6:
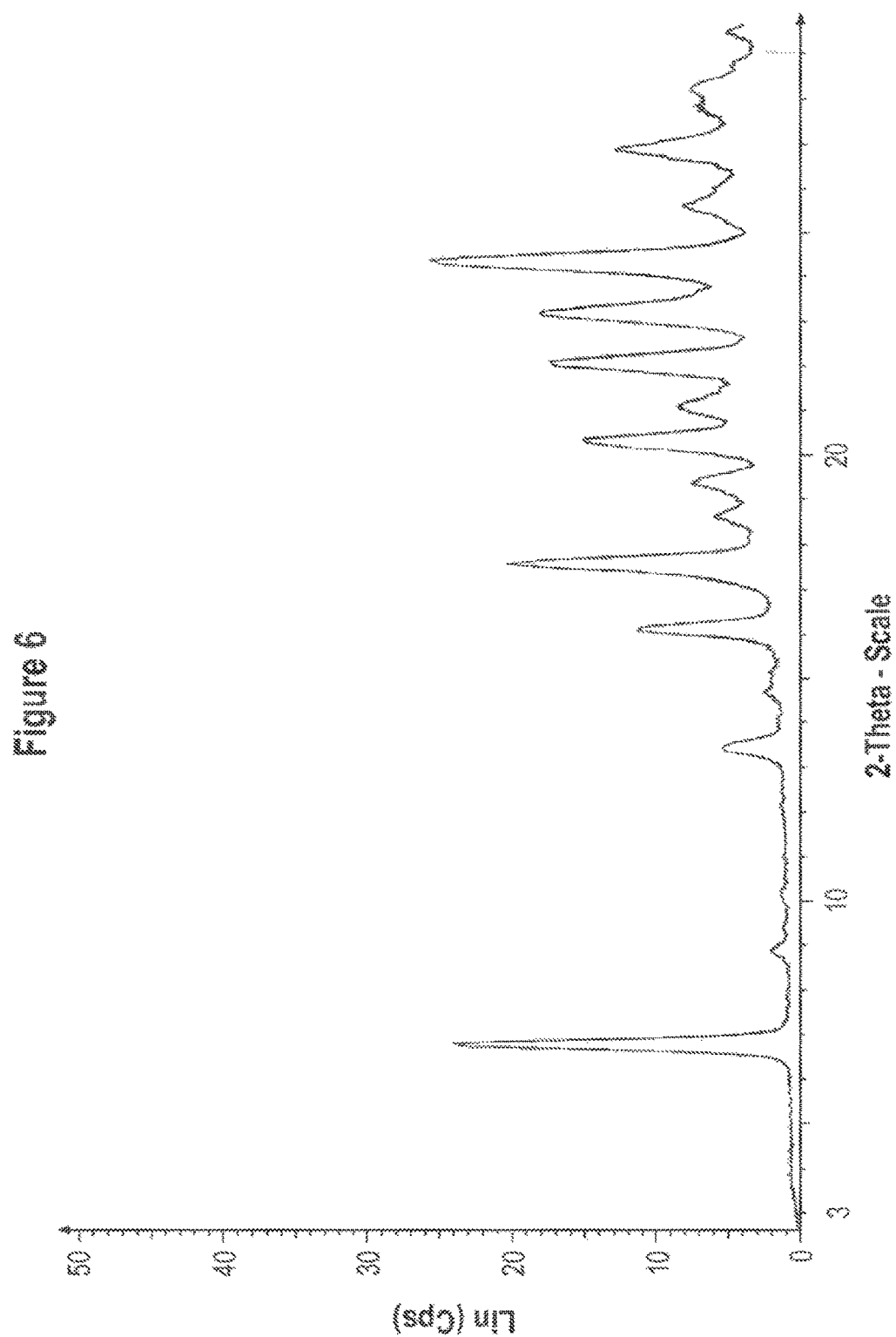
FIG. 6 is an XRPD pattern of Form I (R)-5-((E)-2-pyrrolidin-3-ylvinyl)pyrimidine mono-orotate.

Another embodiment, the present invention includes a polymorphic form of (R)-5-((E)-2-pyrrolidin-3-ylvinyl)pyrimidine mono-orotate Form I whose XRPD pattern substantially corresponds to that shown in FIG. 6.

One embodiment of the present invention includes a crystalline form of (R)-5-((E)-2-pyrrolidin-3-ylvinyl)pyrimidine mono-maleate.

One embodiment of the present invention includes a polymorphic form of (R)-5-((E)-2-pyrrolidin-3-ylvinyl)pyrimidine mono-maleate Form I characterized by a XRPD pattern comprising at least one of the following peaks:

| 2θ |
|---|
| 12.81 |
| 16.09 |
| 18.00 |
| 19.07 |
| 24.49 |
| 26.40 |
| 26.04 |
| 27.88 |

Figure 7:
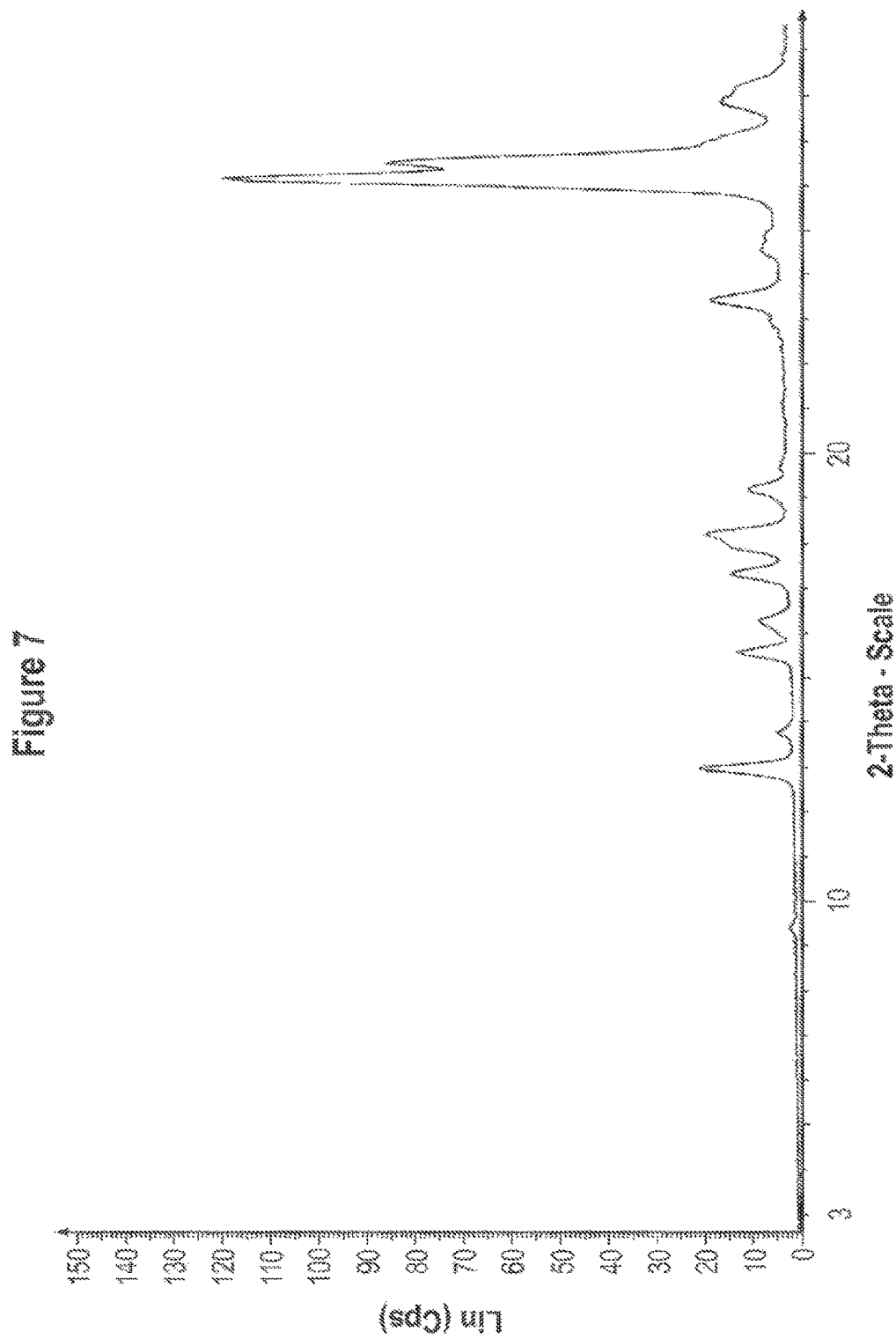
FIG. 7 is an XRPD pattern of Form I (R)-5-((E)-2-pyrrolidin-3-ylvinyl)pyrimidine mono-maleate.

Another embodiment, the present invention includes a polymorphic form of (R)-5-((E)-2-pyrrolidin-3-ylvinyl)pyrimidine mono-maleate Form I whose XRPD pattern substantially corresponds to that shown in FIG. 7.

One embodiment of the present invention includes a polymorphic form of (R)-5-((E)-2-pyrrolidin-3-ylvinyl)pyrimidine mono-maleate Form II characterized by a XRPD pattern comprising at least one of the following peaks:

| 2θ |
|---|
| 4.31 |
| 16.56 |
| 18.29 |
| 18.78 |
| 19.64 |
| 20.27 |
| 21.02 |
| 21.46 |
| 21.90 |
| 22.43 |
| 22.86 |
| 25.40 |
| 25.73 |
| 26.15 |
| 26.56 |
| 27.40 |
| 28.59 |
| 29.57 |

Figure 8:
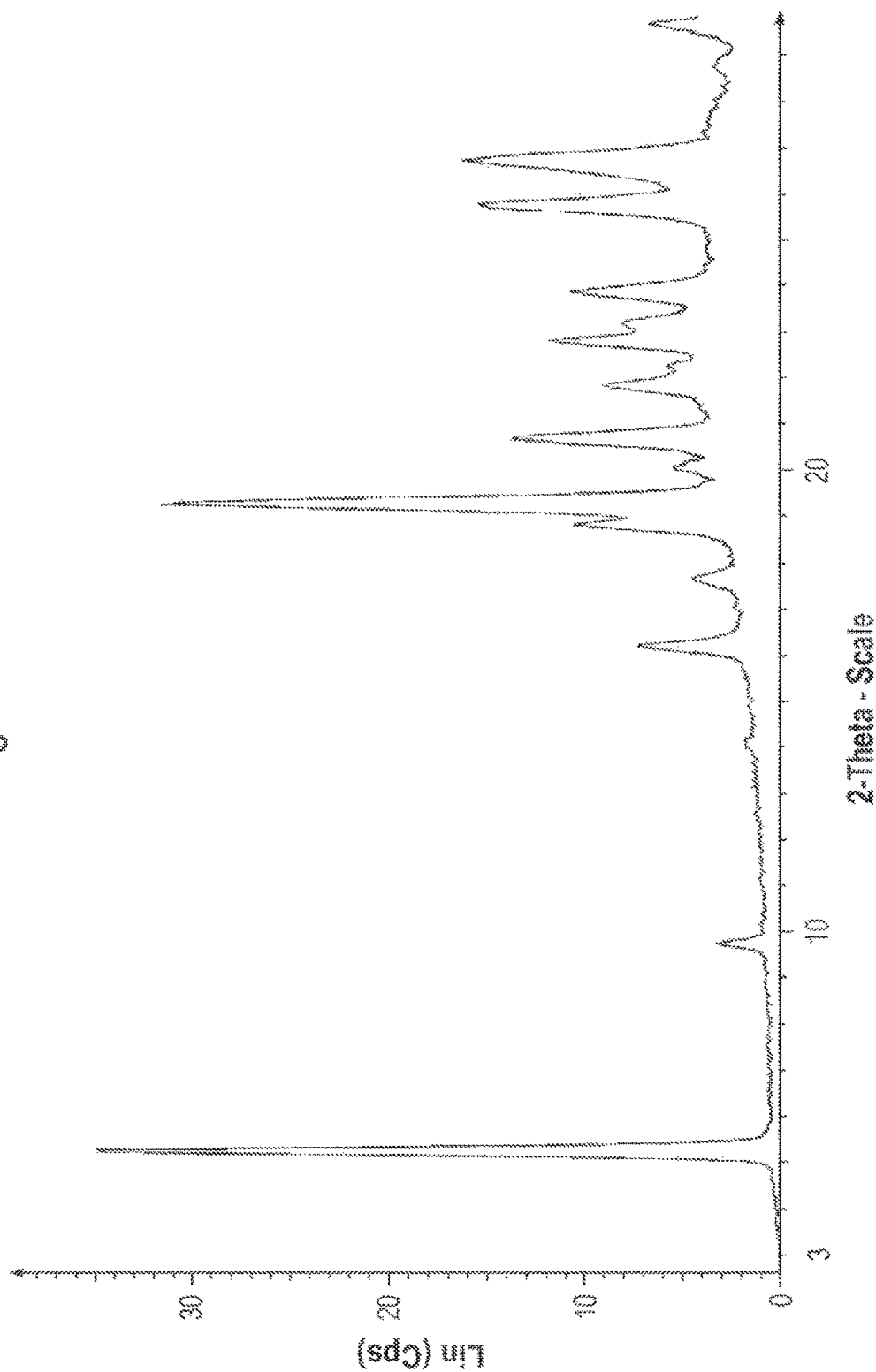
FIG. 8 is an XRPD pattern of Form II (R)-5-((E)-2-pyrrolidin-3-ylvinyl)pyrimidine mono-maleate.

Another embodiment, the present invention includes a polymorphic form of (R)-5-((E)-2-pyrrolidin-3-ylvinyl)pyrimidine mono-maleate Form II whose XRPD pattern substantially corresponds to that shown in FIG. 8

As noted, the salt forms of (R)-5-((E)-2-pyrrolidin-3-ylvinyl)pyrimidine may exist in solvated, for example hydrated, as well as unsolvated forms. The present invention encompasses all such forms.

The present invention also includes isotopically labeled compounds wherein one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine, and chlorine, such as $^2$H, $^3$H, $^{13}$C, $^{14}$C, $^{15}$N, $^{18}$O, and $^{17}$O. Such isotopically labeled compounds are useful as research or diagnostic tools.

Pharmaceutical Compositions

Although it is possible to administer the compound of the present invention in the form of a bulk active chemical, it is preferred to administer the compound in the form of a pharmaceutical composition or formulation. Thus, one aspect the present invention includes pharmaceutical compositions comprising the compound of the present invention and one or more pharmaceutically acceptable carriers, diluents, or excipients. Another aspect of the invention provides a process for the preparation of a pharmaceutical composition, including admixing the compound of the present invention with one or more pharmaceutically acceptable carriers, diluents or excipients.

The manner in which the compound of the present invention is administered can vary. The compound of the present invention is preferably administered orally. Preferred pharmaceutical compositions for oral administration include tablets, capsules, caplets, syrups, solutions, and suspensions. The pharmaceutical compositions of the present invention may be provided in modified release dosage forms such as time-release tablet and capsule formulations.

The pharmaceutical compositions can also be administered via injection, namely, intravenously, intramuscularly, subcutaneously, intraperitoneally, intraarterially, intrathecally, and intracerebroventricularly. Intravenous administration is a preferred method of injection. Suitable carriers for injection are well known to those of skill in the art and include 5% dextrose solutions, saline, and phosphate buffered saline.

The formulations may also be administered using other means, for example, rectal administration. Formulations useful for rectal administration, such as suppositories, are well known to those of skill in the art. The compounds can also be administered by inhalation, for example, in the form of an aerosol; topically, such as, in lotion form; transdermally, such as, using a transdermal patch (for example, by using technology that is commercially available from Novartis and Alza Corporation), by powder injection, or by buccal, sublingual, or intranasal absorption.

Pharmaceutical compositions may be formulated in unit dose form, or in multiple or subunit doses The administration of the pharmaceutical compositions described herein can be intermittent, or at a gradual, continuous, constant or controlled rate. The pharmaceutical compositions may be administered to a warm-blooded animal, for example, a mammal such as a mouse, rat, cat, rabbit, dog, pig, cow, or monkey; but advantageously is administered to a human being. In addition, the time of day and the number of times per day that the pharmaceutical composition is administered can vary.

The compound of the present invention may be used in the treatment of a variety of disorders and conditions and, as such, may be used in combination with a variety of other suitable therapeutic agents useful in the treatment or prophylaxis of those disorders or conditions. Thus, one embodiment of the present invention includes the administration of the compound of the present invention in combination with other therapeutic compounds. For example, the compound of the present invention can be used in combination with other NNR ligands (such as varenicline), antioxidants (such as free radical scavenging agents), antibacterial agents (such as penicillin antibiotics), antiviral agents (such as nucleoside analogs, like zidovudine and acyclovir), anticoagulants (such as warfarin), anti-inflammatory agents (such as NSAIDs), anti-pyretics, analgesics, anesthetics (such as used in surgery), acetylcholinesterase inhibitors (such as donepezil and galantamine), antipsychotics (such as haloperidol, clozapine, olanzapine, and quetiapine), immunosuppressants (such as cyclosporin and methotrexate), neuroprotective agents, steroids (such as steroid hormones), corticosteroids (such as dexamethasone, predisone, and hydrocortisone), vitamins, minerals, nutraceuticals, anti-depressants (such as imipramine, fluoxetine, paroxetine, escitalopram, sertraline, venlafaxine, and duloxetine), anxiolytics (such as alprazolam and buspirone), anticonvulsants (such as phenytoin and gabapentin), vasodilators (such as prazosin and sildenafil), mood stabilizers (such as valproate and aripiprazole), anti-cancer drugs (such as anti-proliferatives), antihypertensive agents (such as atenolol, clonidine, amlopidine, verapamil, and olmesartan), laxatives, stool softeners, diuretics (such as furosemide), anti-spasmotics (such as dicyclomine), anti-dyskinetic agents, and anti-ulcer medications (such as esomeprazole). Such a combination of pharmaceutically active agents may be administered together or separately and, when administered separately, administration may occur simultaneously or sequentially, in any order. The amounts of the compounds or agents and the relative timings of administration will be selected in order to achieve the desired therapeutic effect. The administration in combination of a compound of the present invention with other treatment agents may be in combination by administration concomitantly in: (1) a unitary pharmaceutical composition including both compounds, or (2) separate pharmaceutical compositions each including one of the compounds. Alternatively, the combination may be administered separately in a sequential manner wherein one treatment agent is administered first and the other second. Such sequential administration may be close in time or remote in time.

Another aspect of the present invention includes combination therapy comprising administering to the subject a therapeutically or prophylactically effective amount of the compound of the present invention and one or more other therapy including chemotherapy, radiation therapy, gene therapy, or immunotherapy.

Method of Treatment (R)-5-((E)-2-pyrrolidin-3-ylvinyl)pyrimidine, a pharmaceutically acceptable salt thereof, or a pharmaceutical composition containing such can be used for the prevention or treatment of various conditions or disorders for which other types of nicotinic compounds have been proposed or are shown to be useful as therapeutics, such as CNS disorders, inflammation, inflammatory response associated with bacterial and/or viral infection, pain, metabolic syndrome, autoimmune disorders or other disorders described in further detail herein. This compound can also be used as a diagnostic agent in receptor binding studies (in vitro and in vivo). Such therapeutic and other teachings are described, for example, in references previously listed herein, including Williams et al., Drug News Perspec. 7(4): 205 (1994), Arneric et al., CNS Drug Rev. 1(1): 1-26 (1995), Arneric et al., Exp. Opin. Invest. Drugs 5(1): 79-100 (1996), Bencherif et al., J. Pharmacol. Exp. Ther. 279: 1413 (1996), Lippiello et al., J. Pharmacol. Exp. Ther. 279: 1422 (1996), Damaj et al., J. Pharmacol. Exp. Ther. 291: 390 (1999); Chiari et al., Anesthesiology 91: 1447 (1999), Lavand'homme and Eisenbach, Anesthesiology 91: 1455 (1999), Holladay et al., J. Med. Chem. 40(28): 4169-94 (1997), Bannon et al., Science 279: 77 (1998), PCT WO 94/08992, PCT WO 96/31475, PCT WO 96/40682, and U.S. Pat. No. 5,583,140 to Bencherif et al., U.S. Pat. No. 5,597,919 to Dull et al., U.S. Pat. No. 5,604,231 to Smith et al. and U.S. Pat. No. 5,852,041 to Cosford et al.

CNS Disorders (R)-5-((E)-2-pyrrolidin-3-ylvinyl)pyrimidine, a pharmaceutically acceptable salt thereof, or a pharmaceutical compositions containing such are useful in the treatment or prevention of a variety of CNS disorders, including neurodegenerative disorders, neuropsychiatric disorders, neurologic disorders, and addictions. The compounds and their pharmaceutical compositions can be used to treat or prevent cognitive impairments and dysfunctions, age-related and otherwise; attentional disorders and dementias, including those due to infectious agents or metabolic disturbances; to provide neuroprotection; to treat convulsions and multiple cerebral infarcts; to treat mood disorders, compulsions and addictive behaviors; to provide analgesia; to control inflammation, such as mediated by cytokines and nuclear factor kappa B; to treat inflammatory disorders; to provide pain relief; and to treat infections, as anti-infectious agents for treating bacterial, fungal, and viral infections. Among the disorders, diseases and conditions that the compounds and pharmaceutical compositions of the present invention can be used to treat or prevent are: age-associated memory impairment (AAMI), mild cognitive impairment (MCI), age-related cognitive decline (ARCD), pre-senile dementia, early onset Alzheimer's disease, senile dementia, dementia of the Alzheimer's type, Alzheimer's disease, cognitive impairment no dementia (CIND), Lewy body dementia, HIV-dementia, AIDS dementia complex, vascular dementia, Down syndrome, head trauma, traumatic brain injury (TBI), dementia pugilistica, Creutzfeld-Jacob Disease and prion diseases, stroke, ischemia, attention deficit disorder, attention deficit hyperactivity disorder, dyslexia, schizophrenia, schizophreniform disorder, schizoaffective disorder, cognitive dysfunction in schizophrenia, cognitive deficits in schizophrenia, Parkinsonism including Parkinson's disease, postencephalitic parkinsonism, parkinsonism-dementia of Gaum, frontotemporal dementia Parkinson's Type (FTDP), Pick's disease, Niemann-Pick's Disease, Huntington's Disease, Huntington's chorea, tardive dyskinesia, hyperkinesia, progressive supranuclear palsy, progressive supranuclear paresis, restless leg syndrome, Creutzfeld-Jakob disease, multiple sclerosis, amyotrophic lateral sclerosis (ALS), motor neuron diseases (MND), multiple system atrophy (MSA), corticobasal degeneration, Guillain-Barré Syndrome (GBS), and chronic inflammatory demyelinating polyneuropathy (CIDP), epilepsy, autosomal dominant nocturnal frontal lobe epilepsy, mania, anxiety, depression, premenstrual dysphoria, panic disorders, bulimia, anorexia, narcolepsy, excessive daytime sleepiness, bipolar disorders, generalized anxiety disorder, obsessive compulsive disorder, rage outbursts, oppositional defiant disorder, Tourette's syndrome, autism, drug and alcohol addiction, tobacco addiction, and eating disorders.

Cognitive impairments or dysfunctions may be associated with psychiatric disorders or conditions, such as schizophrenia and other psychotic disorders, including but not limited to psychotic disorder, schizophreniform disorder, schizoaffective disorder, delusional disorder, brief psychotic disorder, shared psychotic disorder, and psychotic disorders due to a general medical conditions, dementias and other cognitive disorders, including but not limited to mild cognitive impairment, pre-senile dementia, Alzheimer's disease, senile dementia, dementia of the Alzheimer's type, age-related memory impairment, Lewy body dementia, vascular dementia, AIDS dementia complex, dyslexia, Parkinsonism including Parkinson's disease, cognitive impairment and dementia of Parkinson's Disease, cognitive impairment of multiple sclerosis, cognitive impairment caused by traumatic brain injury, dementias due to other general medical conditions, anxiety disorders, including but not limited to panic disorder without agoraphobia, panic disorder with agoraphobia, agoraphobia without history of panic disorder, specific phobia, social phobia, obsessive-compulsive disorder, post-traumatic stress disorder, acute stress disorder, generalized anxiety disorder and generalized anxiety disorder due to a general medical condition, mood disorders, including but not limited to major depressive disorder, dysthymic disorder, bipolar depression, bipolar mania, bipolar I disorder, depression associated with manic, depressive or mixed episodes, bipolar II disorder, cyclothymic disorder, and mood disorders due to general medical conditions, sleep disorders, including but not limited to dyssomnia disorders, primary insomnia, primary hypersomnia, narcolepsy, parasomnia disorders, nightmare disorder, sleep terror disorder and sleepwalking disorder, mental retardation, learning disorders, motor skills disorders, communication disorders, pervasive developmental disorders, attention-deficit and disruptive behavior disorders, attention deficit disorder, attention deficit hyperactivity disorder, feeding and eating disorders of infancy, childhood, or adults, tic disorders, elimination disorders, substance-related disorders, including but not limited to substance dependence, substance abuse, substance intoxication, substance withdrawal, alcohol-related disorders, amphetamine or amphetamine-like-related disorders, caffeine-related disorders, *cannabis*-related disorders, cocaine-related disorders, hallucinogen-related disorders, inhalant-related disorders, nicotine-related disorders, opioid-related disorders, phencyclidine or phencyclidine-like-related disorders, and sedative-, hypnotic- or anxiolytic-related disorders, personality disorders, including but not limited to obsessive-compulsive personality disorder and impulse-control disorders.

The above conditions and disorders are discussed in further detail, for example, in the American Psychiatric Association: Diagnostic and Statistical Manual of Mental Disorders, Fourth Edition, Text Revision, Washington, D.C., American Psychiatric Association, 2000.

Inflammation

The nervous system, primarily through the vagus nerve, is known to regulate the magnitude of the innate immune response by inhibiting the release of macrophage tumor necrosis factor (TNF). This physiological mechanism is known as the "cholinergic anti-inflammatory pathway" (see, for example, Tracey, "The inflammatory reflex," *Nature* 420: 853-9 (2002)). Excessive inflammation and tumor necrosis factor synthesis cause morbidity and even mortality in a variety of diseases. These diseases include, but are not limited to, endotoxemia, rheumatoid arthritis, osteoarthritis, psoriasis, asthma, atherosclerosis, idiopathic pulmonary fibrosis, and inflammatory bowel disease.

Inflammatory conditions that can be treated or prevented by administering the compounds described herein include, but are not limited to, chronic and acute inflammation, psoriasis, endotoxemia, gout, acute pseudogout, acute gouty arthritis, arthritis, rheumatoid arthritis, osteoarthritis, allograft rejection, chronic transplant rejection, asthma, atherosclerosis, mononuclear-phagocyte dependent lung injury, idiopathic pulmonary fibrosis, atopic dermatitis, chronic obstructive pulmonary disease, adult respiratory distress syndrome, acute chest syndrome in sickle cell disease, inflammatory bowel disease, irritable bowel syndrome, Crohn's disease, ulcerative colitis, acute cholangitis, aphteous stomatitis, pouchitis, glomerulonephritis, lupus nephritis, thrombosis, and graft vs. host reaction.

Inflammatory Response Associated with Bacterial and/or Viral Infection

Many bacterial and/or viral infections are associated with side effects brought on by the formation of toxins, and the body's natural response to the bacteria or virus and/or the toxins. As discussed above, the body's response to infection often involves generating a significant amount of TNF and/or other cytokines. The over-expression of these cytokines can result in significant injury, such as septic shock (when the bacteria is sepsis), endotoxic shock, urosepsis viral pneumonitis, and toxic shock syndrome.

Cytokine expression is mediated by NNRs, and can be inhibited by administering agonists or partial agonists of these receptors. Those compounds described herein that are agonists or partial agonists of these receptors can therefore be used to minimize the inflammatory response associated with bacterial infection, as well as viral and fungal infections. Examples of such bacterial infections include anthrax, botulism, and sepsis. Some of these compounds may also have antimicrobial properties.

These compounds can also be used as adjunct therapy in combination with existing therapies to manage bacterial, viral and fungal infections, such as antibiotics, antivirals and antifungals. Antitoxins can also be used to bind to toxins produced by the infectious agents and allow the bound toxins to pass through the body without generating an inflammatory response. Examples of antitoxins are disclosed, for example, in U.S. Pat. No. 6,310,043 to Bundle et al. Other agents effective against bacterial and other toxins can be effective and their therapeutic effect can be complemented by co-administration with the compounds described herein.

Pain

The compounds of the present invention and their pharmaceutical compositions are particularly useful in treating and preventing pain, including acute, persistent, and chronic pain. The pain types and painful conditions that can be treated or prevented using the compounds and their pharmaceutical compositions include nociceptive pain, neurologic pain, neuropathic pain, female-specific pain, inflammatory pain, fibromyalgia, post-operative pain, pain due to medical condition (such as AIDS or other disorder), arthritis pain, temporomandibular joint disorder, burn pain, injury pain, back pain, sciatica, foot pain, headache, abdominal pain, muscle and connective tissue pain, joint pain, breakthrough pain, cancer pain, somatic pain, visceral pain, chronic fatigue syndrome, psychogenic pain, and pain disorder.

Neuropathic pain syndromes are the consequence of abnormal changes occurring within pain signaling systems of both the peripheral and central nervous system. Their diverse etiology and symptomatology have traditionally rendered them particularly difficult to treat with any consistency. Examples of neuropathic pain syndromes include those attributed to trigeminal or herpetic neuralgia, peripheral neuropathies (diabetic neuropathy, chemotherapy-induced neuropathy), post-herpetic neuralgia, entrapment neuropathies (carpel-tunnel syndrome), radiculopathy, complex regional pain syndrome, causalgia, low back pain, spontaneous pain (pain without an external stimulus), and deafferentation syndromes such as brachial plexus avulsion and spinal cord injury. Hyperalgesia (strong pain associated with a mild stimulus), allodynia (pain due associated with an innocuous stimulus), parethesias (sensation of numbness or pricking in the absence of an external stimulus), and dysesthesia (spontaneous or evoked unpleasant abnormal sensations) are also typically characterized as types of neuropathic pain. The compounds of the present invention and their pharmaceutical compositions are particularly useful in treating and preventing these neuropathic pain types and associated conditions.

Other Disorders

In addition to treating CNS disorders, inflammation, and pain, the compounds of the present invention can be also used to prevent or treat certain other conditions, diseases, and disorders in which NNRs play a role. Examples include autoimmune disorders such as lupus, disorders associated with cytokine release, cachexia secondary to infection (e.g., as occurs in AIDS, AIDS related complex and neoplasia), obesity, pemphitis, urinary incontinence, retinal diseases, infectious diseases, myasthenia, Eaton-Lambert syndrome, hypertension, osteoporosis, vasoconstriction, vasodilatation, cardiac arrhythmias, type I diabetes, type II diabetes, bulimia, anorexia, diarrhea, constipation, and ulcers, as well as those indications set forth in published PCT application WO 98/25619. The compounds of this invention can also be administered to treat convulsions such as those that are symptomatic of epilepsy, and to treat conditions such as syphillis and Creutzfeld-Jakob disease.

Diagnostic Uses

The compounds can be used in diagnostic compositions, such as probes, particularly when they are modified to include appropriate labels. The probes can be used, for example, to determine the relative number and/or function of specific receptors, particularly the α4β2 receptor subtype. For this purpose the compounds of the present invention most preferably are labeled with a radioactive isotopic moiety such as $^{11}$C, $^{18}$F, $^{76}$Br, $^{123}$I or $^{125}$I.

The administered compounds can be detected using known detection methods appropriate for the label used. Examples of detection methods include position emission topography (PET) and single-photon emission computed tomography (SPECT). The radiolabels described above are useful in PET (e.g., $^{11}$C, $^{18}$F or $^{76}$Br) and SPECT (e.g., $^{123}$I) imaging, with half-lives of about 20.4 minutes for $^{11}$C, about 109 minutes for $^{18}$F, about 13 hours for $^{123}$I, and about 16 hours for $^{76}$Br. A high specific activity is desired to visualize the selected receptor subtypes at non-saturating concentrations. The administered doses typically are below the toxic range and provide high contrast images. The compounds are expected to be capable of administration in non-toxic levels. Determination of dose is carried out in a manner known to one skilled in the art of radiolabel imaging. See, for example, U.S. Pat. No. 5,969,144 to London et al.

The compounds can be administered using known techniques. See, for example, U.S. Pat. No. 5,969,144 to London et al. The compounds can be administered in formulation compositions that incorporate other ingredients, such as those types of ingredients that are useful in formulating a diagnostic composition. Compounds useful in accordance with carrying out the present invention most preferably are employed in forms of high purity. See, U.S. Pat. No. 5,853,696 to Elmalch et al.

After the compounds are administered to a subject (e.g., a human subject), the presence of that compound within the subject can be imaged and quantified by appropriate techniques in order to indicate the presence, quantity, and functionality of selected NNR subtypes. In addition to humans, the compounds can also be administered to animals, such as mice, rats, dogs, and monkeys. SPECT and PET imaging can be carried out using any appropriate technique and apparatus. See Villemagne et al., In: Arneric et al. (Eds.) *Neuronal Nicotinic Receptors: Pharmacology and Therapeutic Opportunities*, 235-250 (1998) and U.S. Pat. No. 5,853,696 to Elmalch et al.

The radiolabeled compounds bind with high affinity to selective NNR subtypes (e.g., α4β2) and preferably exhibit negligible non-specific binding to other nicotinic cholinergic receptor subtypes (e.g., those receptor subtypes associated with muscle and ganglia). As such, the compounds can be used as agents for noninvasive imaging of nicotinic cholinergic receptor subtypes within the body of a subject, particularly within the brain for diagnosis associated with a variety of CNS diseases and disorders.

In one aspect, the diagnostic compositions can be used in a method to diagnose disease in a subject, such as a human patient. The method involves administering to that patient a detectably labeled compound as described herein, and detecting the binding of that compound to selected NNR subtypes (e.g., α4β2 receptor subtypes). Those skilled in the art of using diagnostic tools, such as PET and SPECT, can use the radiolabeled compounds described herein to diagnose a wide variety of conditions and disorders, including conditions and disorders associated with dysfunction of the central and autonomic nervous systems. Such disorders include a wide variety of CNS diseases and disorders, including Alzheimer's disease, Parkinson's disease, and schizophrenia. These and other representative diseases and disorders that can be evaluated include those that are set forth in U.S. Pat. No. 5,952,339 to Bencherif et al.

In another aspect, the diagnostic compositions can be used in a method to monitor selective nicotinic receptor subtypes of a subject, such as a human patient. The method involves administering a detectably labeled compound as described herein to that patient and detecting the binding of that compound to selected nicotinic receptor subtypes namely, the α4β2 receptor subtypes.

Receptor Binding

The compounds of this invention can be used as reference ligands in binding assays for compounds which bind to NNR subtypes, particularly the α4β2 receptor subtypes. For this purpose the compounds of this invention are preferably labeled with a radioactive isotopic moiety such as $^3$H, or $^{14}$C. Examples of such binding assays are described in detail below.

EXAMPLES

The following examples are provided to illustrate the present invention, and should not be construed as limiting thereof. In these examples, all parts and percentages are by weight, unless otherwise noted.

Example 1

Instrumentation and Experimental Protocols for Characterization of Salt Forms of (R)-5-((E)-2-pyrrolidin-3-ylvinyl)pyrimidine X-Ray Powder Diffraction (XRPD)

X-Ray Powder Diffraction patterns were collected on a Bruker AXS C2 GADDS diffractometer using CuKα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. The beam divergence (i.e. the effective size of the X-ray beam on the sample) was approximately 4 mm. A θ-θ continuous scan mode was employed with a sample—detector distance of 20 cm which gives an effective 2θ range of 3.2°-29.7°. Typically the sample would be exposed to the X-ray beam for 120 seconds. Samples run under ambient conditions were prepared as flat plate specimens using powder as received without grinding. Approximately 1-2 mg of the sample was lightly pressed on a glass slide to obtain a flat surface. Samples run under non-ambient conditions were mounted on a silicon wafer with heat-conducting compound. The sample was then heated to the appropriate temperature at ca. 10° C./min and subsequently held isothermally for about 5 min before data collection was initiated. Peak positions are reported as °2θ with an accuracy of ±0.1°.

Single Crystal XRD (SXD)

Data were collected on a Bruker AXS 1K SMART CCD diffractometer equipped with an Oxford Cryosystems Cryostream cooling device. Structures were solved using either the SHELXS or SHELXD programs and refined with the SHELXL program as part of the Bruker AXS SHELXTL suite. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Nuclear Magnetic Resonance (NMR) Spectrometry

NMR spectra were collected on either a Varian Unity 300 MHz instrument or a Bruker 400 MHz instrument equipped with an auto-sampler and controlled by a DRX400 console. Automated experiments were acquired using ICONNMR v4.0.4 (build 1) running with Topspin v 1.3 (patch level 8) using the standard Bruker loaded experiments. For non-routine spectroscopy, data were acquired through the use of Topspin alone.

Melting Point

A Fisher-Johns hot stage melting point apparatus was used, at a setting corresponding to a heating rate of about 5° C. per min.

Differential Scanning Calorimetry (DSC)

DSC data were collected on a TA Instruments Q1000 or a Mettler DSC 823e equipped with a 50 position auto-sampler. The instrument was calibrated for energy and temperature calibration using certified indium. Typically 0.5-1.5 mg of each sample, in a pin-holed aluminium pan, was heated at 10° C./min from 25° C. to 175-200° C. A nitrogen purge at 30 mL/min was maintained over the sample.

Thermo-Gravimetric Analysis (TGA)

TGA data were collected on a TA Instruments Q500 TGA equipped with a 16 position auto-sampler or a Mettler TGA/SDTA 851e equipped with a 34 position auto sampler. TA Instruments Q500: The instrument was temperature calibrated using certified Alumel. Typically 5-10 mg of each sample was loaded onto a pre-tared platinum crucible and aluminium DSC pan, and was heated at 10° C./min from ambient temperature to 350° C. A nitrogen purge at 60 mL/min was maintained over the sample. Mettler TGA/SDTA 851e: The instrument was temperature calibrated using certified indium. Typically 5-10 mg of each sample was loaded onto a pre-tared aluminum crucible and was heated at 10° C./min from ambient temperature to 350° C. A nitrogen purge at 50 mL/min was maintained over the sample.

Polarized Light Microscopy (PLM)

Samples were studied on a Leica LM/DM polarized light microscope with a digital video camera for image capture. A small amount of each sample was placed on a glass slide, mounted in immersion oil and covered with a glass slip, the individual particles being separated as well as possible. The sample was viewed with appropriate magnification and partially polarised light, coupled to a λ false-color filter.

Hot Stage Microscopy (HSM)

Hot Stage Microscopy was carried out using a Leica LM/DM polarized light microscope combined with a Mettler-Toledo MTFP82HT hot-stage and a digital video camera for image capture. A small amount of each sample was placed onto a glass slide with individual particles separated as well as possible. The sample was viewed with appropriate magnification and partially polarized light, coupled to a λ false-color filter, whilst being heated from ambient temperature typically at 10° C./min.

Dynamic Vapor Sorption (DVS)

Sorption isotherms were determined using a SMS DVS Intrinsic moisture sorption analyzer controlled by SMS Analysis suite software. The sample temperature was maintained at 25° C. by the instrument controls. The humidity was controlled by mixing streams of dry and wet nitrogen, with a total flow rate of 200 mL/min. The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg).

Typically a 5-20 mg sample was placed on the tared mesh stainless steel basket under ambient conditions. The sample was loaded and unloaded at 40% RH and 25° C. (typical ambient conditions). A moisture sorption isotherm was performed as outlined below (2 scans giving 1 complete cycle). The standard isotherm was performed at 25° C. at 10% RH intervals over a 0-90% RH range.

DVS Generic Method Parameters

| Parameters | Values |
|---|---|
| Adsorption - Scan 1 | 40-90 |
| Desorption/Adsorption - Scan 2 | 90-Dry, Dry-40 |
| Intervals (% RH) | 10 |
| Number of Scans | 2 |
| Flow rate (mL/min) | 200 |
| Temperature (° C.) | 25 |
| Stability (° C./min) | 0.2 |
| Sorption Time (hours) | 6 hour time out |

Samples were recovered after completion of the isotherm and re-analyzed by XRPD.

Water Determination by Karl Fischer (KF)

The water content of each sample was measured on a Mettler Toledo DL39 Coulometer using Hydranal Coulomat AG reagent and an argon purge. Weighed solid samples were introduced into the vessel on a platinum TGA pan which was connected to a subaseal to avoid water ingress. Approx 10 mg of sample was used per titration and duplicate determinations were made.

Thermodynamic Aqueous Solubility by HPLC

Aqueous solubility was determined by suspending sufficient compound in water to give a maximum final concentration of ≥10 mg/mL of the parent free-form of the compound. The suspension was equilibrated at 25° C. for 24 h, and then the pH was measured. The suspension was then filtered through a glass fiber C filter into a 96 well plate. The filtrate was then diluted by a factor of 101. Quantitation was by HPLC with reference to a standard solution of approximately 0.1 mg/mL in DMSO. Different volumes of the standard, diluted and undiluted sample solutions were injected. The solubility was calculated using the peak areas determined by integration of the peak found at the same retention time as the principal peak in the standard injection. If there was sufficient solid in the filter plate, the XRPD was collected.

HPLC Method Parameters for Thermodynamic Aqueous Solubility Method

| Type of method: | Reverse phase with gradient elution |
|---|---|
| Column: | Phenomenex Luna, C18 (2) 5 µm, 50 × 4.6 mm |
| Column Temperature (° C.): | 25 |
| Standard Injections (µL): | 1, 2, 3, 5, 7, 10 |
| Test Injections (µL): | 1, 2, 3, 10, 20, 50 |
| Detection: Wavelength, Bandwidth (nm): | 260, 80 |
| Flow Rate (mL/min): | 2 |
| Phase A: | 0.1% TFA in water |
| Phase B: | 0.085% TFA in acetonitrile |

| Timetable: | Time (min) | % Phase A | % Phase B |
|---|---|---|---|
| | 0.0 | 95 | 5 |
| | 1.0 | 80 | 20 |
| | 2.3 | 5 | 95 |
| | 3.3 | 5 | 95 |
| | 3.5 | 95 | 5 |
| | 4.4 | 95 | 5 |

Analysis was performed on an Agilent HP1100 series system equipped with a diode array detector and using ChemStation software vB.02.01-SR1.

Chemical Purity by HPLC

Purity analysis was performed on an Agilent HP1100 series system equipped with a diode array detector and using ChemStation software vB.02.01-SR1.

HPLC Method Parameters for Chemical Purity Determination

| Sample Preparation | 0.5 mg/mL in acetonitrile:water 1:1 (v/v) |
|---|---|
| Column: | Phenomenex Luna C18 (2), 150 × 4.6 mm, 5 µm |
| Column Temperature (° C.): | 25 |
| Injection (µL): | 5 |
| Detection: Wavelength, Bandwidth (nm): | 255, 90 |
| Flow Rate (mL/min): | 1 |
| Phase A: | 0.1% TFA in water |
| Phase B: | 0.085% TFA in acetonitrile |

| Timetable: | Time (min) | % Phase A | % Phase B |
|---|---|---|---|
| | 0 | 95 | 5 |
| | 25 | 5 | 95 |
| | 25.2 | 95 | 5 |
| | 30 | 95 | 5 |

Ion Chromatoqraphy

Data were collected on a Metrohm 761 Advanced Compact IC (for cations) and a Metrohm 861 Advanced Compact IC (for anions) using IC Net software v2.3. Samples were prepared as 1000 ppm stocks in DMSO. Samples were diluted to 100 ppm with DMSO prior to testing. Quantification was achieved by comparison with standard solutions of known concentration of the ion being analyzed.

Ion Chromatography Method for Anions

| Type of method | Anion exchange |
|---|---|
| Column: | Metrosep A Supp 5-250 (4.0 × 250 mm) |
| Column Temperature (° C.): | Ambient |
| Injection (µL): | 20 |
| Detection: | Conductivity detector |
| Flow Rate (mL/min): | 0.7 |
| Eluent: | 3.2 mM sodium carbonate, 1.0 mM sodium hydrogen carbonate in water |

Ion Chromatography Method for Cations

| Type of method | Cation exchange |
|---|---|
| Column: | Metrosep C 2-250 (4.0 × 250 mm) |
| Column Temperature (° C.): | Ambient |
| Injection (µL): | 20 |
| Detection: | Conductivity detector |
| Flow Rate (mL/min): | 1.0 |
| Eluent: | 4.0 mM Tartaric acid, 0.75 mM Dipicolinic acid in water | pKa Determination and Prediction

Data were collected on a Sirius GlpKa instrument with a D-PAS attachment. Measurements were made at 25° C. in aqueous solution by UV and in methanol water mixtures by potentiometry. The titration media was ionic-strength adjusted (ISA) with 0.15 M KCl (aq). The values found in the methanol water mixtures were corrected to 0% co-solvent via Yasuda-Shedlovsky extrapolation. The data were refined using Refinement Pro software v1.0. Prediction of pKa values was made using ACD pKa prediction software v9.

Log P Determination

Data were collected by potentiometric titration on a Sirius GlpKa instrument using three ratios of octanol:ionic-strength adjusted (ISA) water to generate Log P, Log $P_{ion}$, and Log D values. The data were refined using Refinement Pro software v1.0. Prediction of Log P values was made using ACD v9 and Syracuse KOWWIN v1.67 software.

Example 2

Synthesis of tert-butyl (R)-3-(methylsulfonyloxy) pyrrolidine-1-carboxylate (2)

Procedure A: To a solution of tert-butyl (R)-3-hydroxypyrrolidine-1-carboxylate (200 g, 1.07 mol) and triethylamine (167 g, 1.63 mol) in toluene (700 mL) at −20 to −30° C. was added methanesulfonyl chloride (156 g, 1.36 mol) drop-wise while maintaining the temperature at −10 to −20° C. The solution was warmed to ambient temperature and allowed to stir. The reaction solution was sampled hourly and analyzed by HPLC to establish completion of the reaction. Upon completion of the reaction, the suspension was filtered to remove the triethylamine hydrochloride. The filtrate was washed with ~600 mL of dilute aqueous sodium bicarbonate solution. The organic layer was dried and concentrated under reduced pressure to give 2 as a viscous oil (260 g, 92%) which is used without further purification. $^1$H NMR (CDCl$_3$, 400 MHz) δ 5.27 (m, 1H), 3.44-3.76 (m, 4H), 3.05 (s, 3H), 2.26 (m, 1H), 2.15 (m, 1H), 1.47 (s, 9H).

Procedure B: A reactor was charged with tert-butyl (R)-3-hydroxypyrrolidine-1-carboxylate (2.00 kg, 10.7 mol), toluene (8.70 kg) and triethylamine (1.75 kg, 17.3 mol). The reactor was flushed with nitrogen for 15 min. The mixture was stirred and cooled to 3° C. Methanesulfonyl chloride (1.72 kg, mol) was slowly added (over a 2 h period) with continuous ice bath cooling (exothermic reaction) (after complete addition, the temperature was 14° C.). The mixture, now viscous with precipitated triethylamine hydrochloride, was stirred 12 h as it warmed to 20° C. Both GC and TLC analysis (ninhydrin stain) indicated that no starting material remained. The mixture was filtered to remove the triethylamine hydrochloride, and the filtrate was returned to the reactor. The filtrate was then washed (2×3 kg) with 5% aqueous sodium bicarbonate, using 15 min of stirring and 15 min of settling time for each wash. The resulting organic layer was dried over anhydrous sodium sulfate and filtered. The volatiles were removed from the filtrate under vacuum, first at 50° C. for 4 h and then at ambient temperature for 10 h. The residue weighed 3.00 kg (106% yield) and was identical by chromatographic and NMR analysis to previously prepared samples, with the exception that it contained toluene.

Example 3

Synthesis of diethyl (R)-2-(1-(tert-butoxycarbonyl) pyrrolidin-3-yl)malonate (3)

Preparation A: To a solution of potassium tert-butoxide (187 g, 1.62 mol) in 1-methyl-2-pyrrolidinone (1.19 L) was added diethyl malonate (268 g. 1.67 mol) while maintaining the temperature below 35° C. The solution was heated to 40° C. and stirred for 20-30 min. tert-Butyl (R)-3-(methylsulfonyloxyl)pyrrolidine-1-carboxylate (112 g, 420 mmol) was added and the solution was heated to 65° C. and stirred for 6 h. The reaction solution was sampled every 2 h and analyzed by HPLC to establish completion of the reaction. Upon completion of reaction (10-12 h), the mixture was cooled to around 25° C. De-ionized water (250 mL) was added to the solution, and the pH was adjusted to 3-4 by addition of 2N hydrochloric acid (650 mL). The resulting suspension was filtered, and water (1.2 L) and chloroform (1.4 L) were added. The solution was mixed thoroughly, and the chloroform layer was collected and evaporated under reduced pressure to give a yellow oil. The oil was dissolved in hexanes (2.00 L) and washed with deionized water (2×1.00 L). The organic layer was concentrated under reduced pressure at 50-55° C. to give a pale yellow oil (252 g) which $^1$H NMR analysis indicates to be 49.1% of 3 (123.8 g) along with 48.5% diethyl malonate (122 g), and 2% of 1-methyl-2-pyrrolidinone (5 g). The material was carried forward to the next step without further purification. $^1$H NMR (CDCl$_3$, 400 MHz) δ 4.20 (q, 4H), 3.63 (m, 1H), 3.48 (m, 1H), 3.30 (m, 1H), 3.27 (d, J=10 Hz, 1H), 3.03 (m, 1H), 2.80 (m, 1H), 2.08 (m, 1H), 1.61 (m, 1H), 1.45 (s, 9H), 1.27 (t, 6H).

Preparation B: A reactor, maintained under a nitrogen atmosphere, was charged with 200 proof ethanol (5.50 kg) and 21% (by weight) sodium ethoxide in ethanol (7.00 kg, 21.6 mol). The mixture was stirred and warmed to 30° C. Diethyl malonate (3.50 kg, 21.9 mol) was added over a 20 min period. The reaction mixture was then warmed at 40° C. for 1.5 h. A solution of tert-butyl (R)-3-(methylsulfonyloxyl) pyrrolidine-1-carboxylate (3.00 kg of the product from Example 2, Procedure B, 10.7 mol) in 200 proof ethanol (5.50 kg) was added, and the resulting mixture was heated at reflux (78° C.) for 2 h. Both GC and TLC analysis (ninhydrin stain) indicated that no starting material remained. The stirred mixture was then cooled to 25° C., diluted with water (2.25 kg), and treated slowly with a solution of concentrated hydrochloric acid (1.27 kg, 12.9 mol) in water (5.44 kg). This mixture was washed twice with methyl tert-butyl ether (MTBE) (14.1 kg and 11.4 kg), using 15 min of stirring and 15 min of settling time for each wash. The combined MTBE washes were dried over anhydrous sodium sulfate (1 kg), filtered and concentrated under vacuum at 50° C. for 6 h. The residue (red oil) weighed 4.45 kg and was 49% desired product by GC analysis (62% overall yield from tert-butyl (R)-3-hydroxypyrrolidine-1-carboxylate).

Example 4

Synthesis of (R)-2-(1-(tert-butoxycarbonyl)pyrrolidin-3-yl)malonic acid (4)

Procedure A: To a solution of the product of Example 3, Procedure A (232 g), containing 123.8 g (380 mmol) of 3 and 121.8 g (760 mmol) of diethyl malonate, in tetrahydrofuran (1.2 L) was added a 21% potassium hydroxide solution (450 g in 0.50 L of deionized water) while maintaining the temperature below 25° C. The reaction mixture was heated to 45° C. and stirred for 1 h. The reaction solution was sampled every hour and analyzed by HPLC to establish completion of the reaction. Upon completion of reaction (2-3 h), the mixture was cooled to around 25° C. The aqueous layer was collected and cooled to 5° C. The pH was adjusted to 2 by addition of 4N hydrochloric acid (750 mL), and the resulting suspension was held at 5-10° C. for 30 min. The mixture was filtered, and the filter cake was washed with hexanes (1 L). The aqueous filtrate was extracted with chloroform (1 L) and the chloroform layer was put aside. The solids collected in the filtration step were re-dissolved in chloroform (1 L) by heating to 40° C. The solution was filtered to remove un-dissolved inorganic solids. The chloroform layers were combined and concentrated under reduced pressure at 50-55° C. to give an off-white solid (15 g). The solids were combined and dissolved in ethyl acetate (350 mL) to give a suspension that was warmed to 55-60° C. for 2 h. The suspension was filtered while hot and the resulting cake washed with ethyl acetate (2×150 mL) and hexanes (2×250 mL) to give 83.0 g (80.1%) of 4 as a white solid which was used in the next step without further purification. $^1$H NMR (d$_4$-CH$_3$OH, 400 MHz) δ 3.60 (m, 1H), 3.46 (m, 1H), 3.29-3.32 (m, 2H), 2.72 (m, 1H), 2.09 (m, 1H), 1.70 (m, 1H), 1.45 (s, 9H).

Procedure B: A solution of the product of Example 3, Procedure B (4.35 kg), containing 2.13 kg (6.47 mol) of 3, in tetrahydrofuran (13.9 kg) was added to a stirred, cooled solution of potassium hydroxide (1.60 kg, 40.0 mol) in deionized water (2.00 kg) under a nitrogen atmosphere, while maintaining the temperature below 35° C. The reaction mixture was heated and maintained at 40-45° C. for 24 h, by which time GC and TLC analysis indicated that the reaction was complete. The mixture was cooled to 25° C. and washed with MTBE (34 kg), using 15 min of stirring and 15 min of settling time. The aqueous layer was collected and cooled to 1° C. A mixture of concentrated hydrochloric acid (2.61 kg, 26.5 mol) in deionized water (2.18 kg) was then added slowly, keeping the temperature of the mixture at <15° C. during and for 15 min after the addition. The pH of the solution was adjusted to 3.7 by further addition of hydrochloric acid. The white solid was collected by filtration, washed with water (16 kg), and vacuum dried at ambient temperature for 6 d. The dry solid weighed 1.04 kg. The filtrate was cooled to <10° C. and kept at that temperature as the pH was lowered by addition of more hydrochloric acid (1.6 L of 6 N was used; 9.6 mol; final pH=2). The white solid was collected by filtration, washed with water (8 L), and vacuum dried at 40° C. for 3 d. The dry solid weighed 0.25 kg. The combined solids (1.29 kg, 73% yield) were chromatographically identical to previously prepared samples.

Example 5

Synthesis of (R)-2-(1-(tert-butoxycarbonyl)pyrrolidine-3-yl)acetic acid (5)

Procedure A: A solution of (R)-2-(1-(tert-butoxycarbonyl)pyrrolidin-3-yl)malonic acid (83 g) in 1-methyl-2-pyrrolidinone (0.42 L) was stirred under nitrogen at 110-112° C. for 2 h. The reaction solution was sampled every hour and analyzed by HPLC to establish completion of the reaction. Upon completion of reaction the reaction solution was cooled to 20-25° C. The solution was mixed with de-ionized water (1.00 L), and MTBE (1.00 L) was added. The phases were separated, and the organic layer was collected. The aqueous phase was extracted with MTBE (1.00 L), then chloroform (1.00 L). The organic layers were combined and concentrated under reduced pressure at 50-55° C. to give an oil. This oil was dissolved in MTBE (2.00 L) and washed twice with 0.6N hydrochloric acid (2×1.00 L). The organic layer was collected and concentrated under reduced pressure at 50-55° C. to give a semi-solid. The semi-solid was suspended in 1:4 ethyl acetate/hexanes (100 mL), heated to 50° C., held for 30 min, cooled to −10° C., and filtered. The filtrate was concentrated under reduced pressure to give an oil, which was dissolved in MTBE (250 mL) and washed twice with 0.6N hydrochloric acid (2×100 mL). The organic layer was concentrated under reduced pressure at 50-55° C. to give a semi-solid which was suspended in 1:4 ethyl acetate/hexanes (50 mL), heated to 50° C., held for 30 min, cooled to −10° C., and filtered. The solids were collected, suspended in hexanes (200 mL), and collected by filtration to give 54.0 g (77.6%) of 5. $^1$H NMR (CDCl$_3$, 400 MHz) δ 11.00 (br s, 1H), 3.63 (m, 1H), 3.45 (M, 1H), 3.30 (M, 1H), 2.97 (m, 1H), 2.58 (m, 1H), 2.44 (m, 2H), 2.09 (m, 1H), 1.59 (M, 1H), 1.46 (s, 9H).

Procedure B: A solution of (R)-2-(1-(tert-butoxycarbonyl) pyrrolidin-3-yl)malonic acid (1.04 kg, 3.81 mol) in 1-methyl-2-pyrrolidinone (6.49 kg) was stirred under nitrogen at 110° C. for 5 h, by which time TLC and HPLC analysis indicated that the reaction was complete. The reaction mixture was cooled to 25° C. (4 h) and combined with water (12.8 kg) and MTBE (9.44 kg). The mixture was stirred vigorously for 20 min, and the phases were allowed to separate (10 h). The organic phase was collected, and the aqueous phase was combined with MTBE (9.44 kg), stirred for 15 min, and allowed to settle (45 min). The organic phase was collected, and the aqueous phase was combined with MTBE (9.44 kg), stirred for 15 min, and allowed to settle (15 min). The three organic phases were combined and washed three times with 1N hydrochloric acid (8.44 kg portions) and once with water (6.39 kg), using 15 min of stirring and 15 min of settling time for each wash. The resulting solution was dried over anhydrous sodium sulfate (2.0 kg) and filtered. The filtrate was concentrated under reduced pressure at 31° C. (2 h) to give an solid. This solid was heated under vacuum for 4 h at 39° C. for 4 h and for 16 h at 25° C., leaving 704 g (81%) of 5 (99.7% purity by GC).

Procedure C: (streamlined synthesis of 5, using 2 as starting material): A stirred mixture of sodium ethoxide in ethanol (21 weight percent, 343 g, 1.05 mol), ethanol (anhydrous, 300 mL) and diethyl malonate (168 g, 1.05 mol) was heated to 40° C. for 1.5 h. To this mixture was added a solution of (R)-tert-butyl 3-(methylsulfonyloxy)pyrrolidine-1-carboxylate (138 g, 0.592 mol) in ethanol (100 mL) and the reaction mixture was heated to 78° C. for 8 h. The cooled reaction mixture was diluted with water (2.0 L) and acidified to pH=3 with 6M HCl (100 mL). The aqueous ethanol mixture was extracted with toluene (1.0 L), and the organic phase concentrated under vacuum to afford 230 g of a red oil. The red oil was added at 85° C. to a 22.5 weight percent aqueous potassium hydroxide (748 g, 3.01 mol). After the addition was complete, the reaction temperature was allowed to slowly rise to 102° C. while a distillation of ethanol ensued. When the reaction temperature had reached 102° C., and distillation had subsided, heating was continued for an additional 90 min. The reaction mixture was cooled to ambient temperature and washed with toluene (2×400 mL). To the aqueous layer was added 600 mL 6M hydrochloric acid, while keeping the internal temperature below 20° C. This resulted in the formation of a precipitate, starting at pH of about 4-5. The suspension was filtered, and the filter cake was washed with 300 mL water. The solid was dried under vacuum to afford 77 g of (R)-2-(1-(tert-butoxycarbonyl)pyrrolidin-3-yl)malonic acid as an off-white solid (54% yield with respect to (R)-tert-butyl 3-(methylsulfonyloxy)pyrrolidine-1-carboxylate). $^1$H NMR (DMSO-d$_6$, 400 MHz): δ 3.47 (m, 1H); 3.32 (m, 1H); 3.24 (m, 1H); 3.16 (m, 1H); 3.92 (m, 1H); 2.86 (m, 1H); 1.95 (m, 1H); 1.59 (m, 1H); 1.39 (s, 9H).

A suspension of (R)-2-(1-(tert-butoxycarbonyl)pyrrolidin-3-yl)malonic acid (15 g, 55 mmol) in toluene (150 mL) and dimethylsulfoxide (2 mL) was heated to reflux for a period of 2 h. The mixture was allowed to reach ambient and diluted with MTBE (150 mL). The organic solution was washed with 10% aqueous citric acid (2×200 mL), and the solvent was removed under vacuum to afford 11.6 g of (R)-2-(1-(tert-butoxycarbonyl)-pyrrolidin-3-yl)acetic acid as an off-white solid (92% yield). $^1$H NMR (DMSO-d$_6$, 400 MHz): b 12.1 (s, 1H); 3.36-3.48 (m, 1H); 3.20-3.34 (m, 1H); 3.05-3.19 (m, 1H; 2.72-2.84 (m, 1H); 2.30-2.42 (m, 1H), 2.22-2.30 (m, 2H); 1.85-2.00 (m, 1H); 1.38-1.54 (m, , 1H), 1.35 (2, 9H).

Example 6

Synthesis of tert-butyl (R)-3-(2-hydroxyethyl)pyrrolidine-1-carboxylate (6)

Procedure A: A solution of (R)-2-(1-(tert-butoxycarbonyl)pyrrolidine-3-yl)acetic acid (49.0 g, 214 mmol) in tetrahydrofuran (THF) (200 mL) was cooled to −10° C. 250 mL (250 mmol) of a 1M borane in THF solution was added slowly to the flask while maintaining the temperature lower than 0° C. The solution was warmed to ambient temperature and stirred for 1 h. The solution was sampled hourly and analyzed by HPLC to establish completion of the reaction. Upon completion of the reaction, the solution was cooled to 0° C., and a 10% sodium hydroxide solution (80 mL) was added drop-wise over a 30 minute period to control gas evolution. The solution was extracted with 500 mL of a 1:1 hexanes/ethyl acetate solution. The organic layer was washed with saturated sodium chloride solution and dried with 10 g of silica gel. The silica gel was removed by filtration and washed with 100 mL of 1:1 hexanes/ethyl acetate. The organic layers were combined and concentrated under vacuum to give 6 (42 g, 91.3%) as a light-orange oil that solidified upon sitting. $^1$H NMR (CDCl$_3$, 400 MHz) δ 3.67 (m, 2H), 3.38-3.62 (m, 2H), 3.25 (m, 1H), 2.90 (m, 1H), 2.25 (m, 1H), 1.98-2.05 (m, 1H), 1.61-1.69 (m, 2H), 1.48-1.59 (m, 2H), 1.46 (s, 9H).

Procedure B: Borane-THF complex (3.90 kg or L of 1M in THF, mol) was added slowly to a stirred solution of (R)-2-(1-(tert-butoxycarbonyl)pyrrolidine-3-yl)acetic acid (683 g, 3.03 mol) in THF (2.5 kg), kept under nitrogen gas, and using a water bath to keep the temperature between 23 and 28° C. The addition took 1.75 h. Stirring at 25° C. was continued for 1 h, after which time GC analysis indicated complete reaction. The reaction mixture was cooled to <10° C. and maintained below 25° C. as 10% aqueous sodium hydroxide (1.22 kg) was slowly added. The addition took 40 min. The mixture was stirred 1 h at 25° C., and then combined with 1:1 (v/v) heptane/ethyl acetate (7 L). The mixture was stirred for 15 min and allowed to separate into phases (1 h). The organic phase was withdrawn, and the aqueous phase was combined with a second 7 L portion of 1:1 heptane/ethyl acetate. This was stirred for 15 min and allowed to separate into phases (20 min). The organic phase was again withdrawn, and the combined organic phases were washed with saturate aqueous sodium chloride (4.16 kg), using 15 min of mixing and 1 h of settling time. The organic phase was combined with silica gel (140 g) and stirred 1 h. The anhydrous sodium sulfate (700 g) was added, and the mixture was stirred for 1.5 h. The mixture was filtered, and the filter cake was washed with 1:1 heptane/ethyl acetate (2 L). The filtrate was concentrated under vacuum at <40° C. for 6 h. The resulting oil weighed 670 g (103% yield) and contains traces of heptane, but is otherwise identical to previously prepared samples of 6, by NMR analysis.

Example 7 tert-butyl (R)-3-(2-(methylsulfonyloxy)ethyl)pyrrolidine-1-carboxylate (7)

Procedure A: To a solution of tert-butyl (R)-3-(2-hydroxymethyl)pyrrolidine-1-carboxylate (41.0 g, 190 mmol)) was added triethylamine (40 mL) in toluene (380 mL) and cooled to −10° C. Methanesulfonyl chloride (20.0 mL, 256 mmol) was added slowly so as to maintain the temperature around −5 to 0° C. The solution was warmed to ambient temperature and stirred for 1 h. The solution was sampled hourly and analyzed by HPLC to establish completion of the reaction. Upon completion of reaction, the solution was filtered, and the filtrate was washed with a 5% sodium bicarbonate solution (250 mL). The organic layer was collected and washed with a saturated aqueous sodium chloride solution (250 mL). The organic layer was collected, dried over silica gel (10 g), and concentrated under vacuum to give 7 (53.0 g, 92.8%) as a light-yellow viscous oil. $^1$H NMR (CDCl$_3$, 400 MHz) δ 4.26 (t, J=6.8 Hz, 2H), 3.41-3.63 (m, 2H), 3.27 (m, 1H), 3.02 (s, 3H), 2.92 (m, 1H), 2.28 (m, 1H), 2.05 (m, 1H), 1.83 (m, 2H), 1.50-1.63 (m, 1H), 1.46 (s, 9H).

Procedure B: Under a nitrogen atmosphere, a solution of triethylamine (460 g, 4.55 mol) and tert-butyl (R)-3-(2-hydroxymethyl)pyrrolidine-1-carboxylate (the entire sample from Example 7, Procedure B, 3.03 mol) in toluene (5.20 kg) was stirred and cooled to 5° C. Methanesulfonyl chloride (470 g, 4.10 mol) was added slowly, over a 1.25 h, keeping the temperature below 15° C. using ice bath cooling. The mixture was gradually warmed (over 1.5 h) to 35° C., and this temperature was maintained for 1.25 h, at which point GC analysis indicated that the reaction was complete. The mixture was cooled to 25° C., and solids were filtered off and the filter cake washed with toluene (1.28 kg). The filtrate was stirred with 10% aqueous sodium bicarbonate (4.0 kg) for 15 min, and the phases were allowed to separate for 30 min. The organic phase was then stirred with saturated aqueous sodium chloride (3.9 kg) for 30 min, and the phases were allowed to separate for 20 min. The organic phase was combined with silica gel (160 g) and stirred for 1 h. Anhydrous sodium sulfate (540 g) was added, and the mixture was stirred an additional 40 min. The mixture was then filtered, and the filter cake was washed with toluene (460 g). The filtrate was concentrated under vacuum at 50° C. for 5 h, and the resulting oil was kept under vacuum at 23° C. for an additional 8 h. This left 798 g of 7, 93% pure by GC analysis.

Example 8

Synthesis of tert-butyl (R)-3-vinylpyrrolidine-1-carboxylate (9)

Procedure A: A solution of tert-butyl (R)-3-((methylsulfonyloxy)ethyl)pyrrolidine-1-carboxylate (49.0 g, 167 mmol), sodium iodide (30.0 g, 200 mmol) and 1,2-dimethoxyethane (450 mL) was stirred at 50-60° C. for 4 h. The solution was sampled hourly and analyzed by HPLC to establish completion of the reaction. Upon completion of reaction, the solution was cooled to −10° C., and solid potassium tert-butoxide (32.0 g, 288 mmol) was added while maintaining temperature below 0° C. The reaction mixture was warmed to ambient temperature and stirred for 1 h. The mixture was sampled hourly and analyzed by HPLC to establish completion of the reaction. Upon completion of reaction, the mixture was filtered through a pad of diatomaceous earth (25 g dry basis). The cake was washed with 1,2-dimethoxyethane (100 mL). The combined filtrates were concentrated under vacuum, to yield an orange oil with suspended solids. The oil was dissolved in hexanes (400 mL), stirred for 30 min, and filtered to remove the solids. The organic layer was dried over silica gel (10 g), and concentrated under vacuum to give 9 (26.4 g, 82.9%) as a colorless oil. $^1$H NMR (CDCl$_3$, 400 MHz) δ 5.77 (m, 1H), 5.10 (dd, J=1.2 Hz, J=16 Hz, 1H), 5.03 (dd, J=1.2 Hz, J=8.8 Hz, 1H), 3.41-3.59 (m, 2H), 3.29 (m, 1H), 3.05 (m, 1H), 2.78 (m, 1H), 2.01 (m, 1H), 1.62-1.73 (m, 1H), 1.46 (m, 9H).

Procedure B: A solution of tert-butyl (R)-3-(2-(methylsulfonyloxy)ethyl)pyrrolidine-1-carboxylate (792 g of the product of Example 7, Procedure B, ~2.5 mol), sodium iodide (484 g, 3.27 mol) and 1,2-dimethoxyethane (7.2 L) was stirred at 55° C. for 4.5 h under nitrogen, at which time GC analysis indicated that the reaction was complete. The solution was cooled to <10° C., and solid potassium tert-butoxide (484 g, 4.32 mol) was added in portions (1.25 h addition time) while maintaining temperature below 15° C. The reaction mixture was stirred 1 h at 5° C., warmed slowly (6 h) to 20° C., and stirred at 20° C. for 1 h. The solution was filtered through a pad of diatomaceous earth (400 g dry basis). The filter cake was washed with 1,2-dimethoxyethane (1.6 kg). The combined filtrates were concentrated under vacuum, and the semisolid residue was stirred with heptane (6.0 L) for 2 h. The solids were removed by filtration (the filter cake was washed with 440 mL of heptane), and the filtrate was concentrated under vacuum at 20° C. to give 455 g of 9 (90.7% pure). A sample of this material (350 g) was fractionally distilled at 20-23 torr to give 296 g of purified 9 (bp 130-133° C.) (>99% pure by GC analysis).

Example 9

Synthesis of (R)-5-((E)-2-pyrrolidin-3-ylvinyl)pyrimidine (11)

Nitrogen was bubbled through a solution of (R)-tert-butyl 3-vinylpyrrolidine-1-carboxylate (25 g, 127 mmol), 5-bromopyrimidine (30.3 g, 190 mmol), 1,1'-bis(diphenylphosphino)ferrocene (2.11 g, 3.8 mmol), and sodium acetate (18.8 gr, 229 mmol) in N,N-dimethylacetamide (250 mL) for 1 h, and palladium acetate (850 mg, 3.8 mmol) was added. The reaction mixture was heated to 150° C. at a rate of 40° C./h and stirred for 16 h. The mixture was cooled to 10° C. and quenched with water (750 mL) while maintaining an internal temperature below 20° C. MTBE (300 mL) was added, followed by diatomaceous earth (40 g, dry basis). The suspension was stirred for 1 h at ambient temperature and filtered through a bed of diatomaceous earth. The residue was washed with MTBE (2×100 mL) and the filtrate was transferred to a 2-L vessel equipped with an overhead stirrer and charged with activated charcoal (40 g). The suspension was stirred for 2 h at ambient temperature and filtered through diatomaceous earth. The residue was washed with MTBE (2×100 mL,), and the filtrate was concentrated in vacuo to afford 28.6 g of an orange oil. The oil is dissolved in MTBE (100 mL) and Si-Thiol® (2.0 g, 1.46 mmol thiol/g, Silicycle Inc.) was added. The suspension was stirred under nitrogen at ambient temperature for 3 h, filtered through a fine filter, and held in a glass container.

To a solution of 6 M HCl (70 mL) was added the filtrate over a period of 30 min while maintaining the internal temperature between 20° C. and 23° C. The mixture was stirred vigorously for 1 h and the organic layer removed. The remaining aqueous layer was basified with 45 wt % KOH (50 mL), and the resulting suspension was extracted once with chloroform (300 mL). Evaporation of the solvent in vacuo (bath temperature at 45° C.) gave 16.0 g (71.8%), of (R)-5-((E)-2-pyrrolidin-3-ylvinyl)pyrimidine free base as a red oil, which is immediately dissolved in isopropanol (50 mL) and used for salt formation.

Example 10

Synthesis of (R)-5-((E)-2-pyrrolidin-3-ylvinyl)pyrimidine mono-citrate

To a solution of citric acid (17.6 g, 91.6 mmol) in isopropanol (250 mL) and water (25 mL) was added dropwise a solution of (R)-5-((E)-2-pyrrolidin-3-ylvinyl)pyrimidine free base (16.0 g, 91.2 mmol) in isopropanol (50 mL) at 55° C. The resulting solution was seeded with (R)-5-((E)-2-pyrrolidin-3-ylvinyl)pyrimidine mono-citrate Form II (200 mg) and stirred for 15 min. The suspension was heated to 65° C. and stirred for 1 h, after which the suspension was cooled to 20° C. at −10° C./h and allowed to stand at 20° C. for 12 h. The suspension was filtered through a coarse glass filter, and the collected solid was washed with isopropanol (64 mL) and methyl tert-butyl ether (64 mL). The resulting, free-flowing, tan solid was dried in vacuo at 70° C. to give 17.4 g (36%) of (R)-5-((E)-2-pyrrolidin-3-ylvinyl)pyrimidine mono-citrate (mixture of Forms II and III) as a tan solid. $^1$H NMR (D$_2$O, 400 MHz) δ: 8.85 (s, 1H), 8.70 (s, 1H), 6.50 (d, J=17 Hz, 1H), 6.35 (dd, J=7 Hz, J=17 Hz, 1H), 3.43-3.50 (m, 1H), 3.34-3.43 (m, 1H), 3.20-3.30 (m, 1H), 3.08-3.19 (m, 1H), 3.00-3.08 (m, 1H), 2.77 (d; J=16 Hz, 2H), 2.65 (d, J=16 Hz, 2H), 2.16-2.26 (m, 1H), 1.80-1.92 (m, 1H).

Example 11

Screen for hydrochloric acid addition salts of (R)-5-((E)-2-pyrrolidin-3-ylvinyl)pyrimidine (R)-5-((E)-2-Pyrrolidin-3-ylvinyl)pyrimidine free base was dissolved in either, isopropyl acetate, tetrahydrofuran, methyl isobutyl ketone, acetonitrile, or isopropyl alcohol. The resulting solution was treated with 1 eq. of HCl delivered in one of the following forms: 1M in diethyl ether, 1M in water, 5M in isopropyl alcohol or 4M in dioxane. The mixture was incubated at 50° C./ambient temperature (4 h cycles) for 24 h. Where the experiment resulted in a stable solid, the material was analyzed by XRPD.

Example 12

Screen for "mono" acid addition salts of (R)-5-((E)-2-pyrrolidin-3-ylvinyl)pyrimidine (R)-5-((E)-2-Pyrrolidin-3-ylvinyl)pyrimidine free base (10 mg, 0.057 mmol) was dissolved in either isopropyl acetate or acetonitrile. The solutions were treated with 1 eq. of the corresponding acid (see below), warmed to 50° C., and cooled slowly to ambient temperature overnight. The solvent was then evaporated under vacuum without heating, and the residues analyzed by XRPD. The solids are then stored in a humidity chamber at 40° C. and 75% RH for a week, and re-analyzed by XRPD.

In the cases where the experiment did not yield a crystalline solid, the samples were matured in tetrahydrofuran and isopropyl alcohol, and where a solid was obtained, the solid was analyzed by XRPD and stored in the humidity chamber for a week to assess stability.

The following acids were screened, using the above procedures for forming "mono" acid addition salts: hydrochloric acid, sulfuric acid, methanesulfonic acid, maleic acid, phosphoric acid, 1-hydroxy-2-naphthoic acid, ketoglutaric acid, malonic acid, L-tartaric acid, fumaric acid, citric acid, L-malic acid, hippuric acid, L-lactic acid, benzoic acid, succinic acid, adipic acid, acetic acid, nicotinic acid, propionic acid, orotic acid, 4-hydroxybenzoic acid, and di-p-Toluoyl-D-tartaric acid.

Example 13

Screen for "hemi" acid addition salts of (R)-5-((E)-2-pyrrolidin-3-ylvinyl)pyrimidine (R)-5-((E)-2-Pyrrolidin-3-ylvinyl)pyrimidine free base (10 mg, 0.057 mmol) was dissolved in either isopropyl acetate or acetonitrile. The solutions were then treated with 0.5 eq. of the corresponding acid (see below), warmed to 50° C., and cooled slowly to ambient temperature overnight. The solvent was then evaporated under vacuum without heating, and the residues analyzed by XRPD. The solids were then stored in the humidity chamber at 40° C. and 75% RH for a week, and re-analyzed by XRPD.

In the cases where the experiment did not yield a crystalline solid, these samples were matured in tetrahydrofuran and isopropyl alcohol, and where a solid was obtained, the solid is analyzed by XRPD and stored in the humidity chamber for a week to assess stability.

The following acids were screened, using the above procedures for forming "hemi" acid addition salts: sulfuric acid, maleic acid, phosphoric acid, ketoglutaric acid, malonic acid, L-tartaric acid, fumaric acid, citric acid, L-malic acid, succinic acid, adipic acid, and di-p-toluoyl-D-tartaric acid.

Example 14

General scale-up procedure for selected salts of (R)-5-((E)-2-pyrrolidin-3-ylvinyl)pyrimidine A number of (R)-5-((E)-2-pyrrolidin-3-ylvinyl)pyrimidine salts were
chosen to scale-up to ~200 mg for further characterization. These salt forms include: citrate (mono and hemi), orotate (mono), 4-hydroxybenzoate (mono), di-p-toluoyl-D-tartrate (mono and hemi), maleate (mono and hemi), and fumarate (mono and hemi).

(R)-5-((E)-2-pyrrolidin-3-ylvinyl)pyrimidine free base (189 mg, 1.077 mmol) was dissolved in acetonitrile. The solution was then treated with 1.1 eq. of the corresponding acid for the preparation of the mono salt, and 0.5 eq. for the preparation of the hemi salt. The mixture was warmed up to 50° C. and cooled down slowly to ambient temperature overnight.

The solid obtained was filtered and dried under suction before being analyzed by XRPD, and $^1$H-NMR. TGA experiments were performed to determine content of water or other solvents, and DSC experiments were run to establish stability of the isolated forms and the possibility of new forms for each salt. DVS experiments were used to assess hygroscopicity of the salts. HPLC purity and thermodynamic solubility were also measured for each salt.

Example 15

(R)-5-((E)-2-Pyrrolidin-3-ylvinyl)pyrimidine mono-citrate Form I (R)-5-((E)-2-Pyrrolidin-3-ylvinyl)pyrimidine mono-citrate Form I was obtained according to the mono salt screening procedure, from isopropyl acetate, by evaporation and maturation in tetrahydrofuran. Alternatively, the mono-citrate Form I was obtained according to the mono salt screening procedure, from acetonitrile, by evaporation and maturation in isopropyl alcohol. The XRPD diffractogram of (R)-5-((E)-2-pyrrolidin-3-ylvinyl)pyrimidine mono-citrate Form I is shown in FIG. 2.

Example 16

(R)-5-((E)-2-Pyrrolidin-3-ylvinyl)pyrimidine mono-citrate Form II

A suspension of the (R)-5-((E)-2-pyrrolidin-3-ylvinyl) pyrimidine mono-citrate Forms II and III mixture in methanol was heated to 50° C. and stirred for 1 h. The suspension was subsequently cooled to 20° C. at a rate of −30° C./h, followed immediately by heating back to 50° C. at a rate of +30° C./h. Heating was discontinued upon reaching 50° C., and the suspension was cooled and stirred at ambient temperature for 16 h. The suspension was filtered, and any residual material in the flask was rinsed out with additional methanol. The residue was dried at 70° C. in vacuo for 16 h to give (R)-5-((E)-2-pyrrolidin-3-ylvinyl)pyrimidine mono-citrate Form II. The XRPD diffractogram of (R)-5-((E)-2-pyrrolidin-3-ylvinyl)pyrimidine mono-citrate Form II is shown in FIG. 3.

Example 17

Amorphous (R)-5-((E)-2-pyrrolidin-3-ylvinyl)pyrimidine mono-citrate

Amorphous (R)-5-((E)-2-pyrrolidin-3-ylvinyl)pyrimidine mono-citrate was prepared by freeze drying a solution of (R)-5-((E)-2-pyrrolidin-3-ylvinyl)pyrimidine mono-citrate Form II in water. The XRPD diffractogram of amorphous (R)-5-((E)-2-pyrrolidin-3-ylvinyl)pyrimidine mono-citrate is shown in FIG. 1.

Example 18

(R)-5-((E)-2-Pyrrolidin-3-ylvinyl)pyrimidine mono-citrate Form III (R)-5-((E)-2-pyrrolidin-3-ylvinyl)pyrimidine mono-citrate Form III was prepared by allowing amorphous (R)-5-((E)-2-pyrrolidin-3-ylvinyl)pyrimidine mono-citrate to stand at ambient temperature for two hours. The XRPD diffractogram of (R)-5-((E)-2-pyrrolidin-3-ylvinyl)pyrimidine mono-citrate Form III is shown in FIG. 4.

Example 19

(R)-5-((E)-2-Pyrrolidin-3-ylvinyl)pyrimidine mono-citrate Form IV (R)-5-((E)-2-Pyrrolidin-3-ylvinyl)pyrimidine mono-citrate Form IV was obtained by maturation of Form II in acetone/methyl isobutyl ketone. The XRPD diffractogram of mono-citrate Form IV is shown in FIG. 5.

Example 20

(R)-5-((E)-2-Pyrrolidin-3-ylvinyl)pyrimidine mono-(R)-(−)-orotate salt

Orotic acid (0.965 g, 6.18 mmol) was added as a solid to a stirring, hot solution of (R)-5-((E)-2-pyrrolidin-3-ylvinyl)

pyrimidine free base (1.084 g, 6.18 mmol) in 2-propanol (10 mL) in a round-bottomed flask. The resulting mixture of solids was heated under reflux for 5 min, cooled to ambient temperature and stirred overnight. The light-beige powder was filtered, washed with 2-propanol (10, 8 mL) and dried in a vacuum oven (air bleed) at 50° C. for 20 h to give 1.872 g (77.9%) of an off-white to white, lumpy solid, mp 230-233° C. $^1$H NMR (D$_2$O): δ 8.80 (s, 1H), 8.60 (s, 2H), 6.40 (d, 1H), 6.25 (dd, 1H), 5.93 (s, 1H, =CH of orotic acid, indicating a mono-salt stoichiometry), 3.38 (dd, 1H), 3.29 (m, 1H), 3.17 (m, 1H), 3.04 (m, 1H), 2.97 (dd, 1H), 2.13 (m, 1H), 1.78 (m, 1H). Elemental analysis results suggests the presence of excess orotic acid and a 1:1.1 base:orotic acid salt stoichiometry. Elemental Analysis: Calculated for $C_{10}H_{13}N_3 \cdot C_5H_4N_2O_4$: (C, 54.38%; H, 5.17%, N, 21.14%); Found: (C, 53.49%, 53.44%; H, 5.04%, 5.10%; N, 20.79%, 20.84%).

Example 21

(R)-5-((E)-2-Pyrrolidin-3-ylvinyl)pyrimidine mono-orotate Form I (R)-5-((E)-2-pyrrolidin-3-ylvinyl)pyrimidine free base (189 mg, 1.077 mmol, freshly prepared) was dissolved in acetonitrile (5 ml). The solution was then treated with 1.1 eq. of an orotic acid solution (1M in ethanol) at ambient temperature. The mixture was warmed up to 50° C. and cooled down slowly to ambient temperature overnight. The solid obtained was filtered and dried under suction before being analysed by XRPD, and $^1$H-NMR. The XRPD diffractogram of (R)-5-((E)-2-pyrrolidin-3-ylvinyl)pyrimidine mono-orotate Form I is shown in FIG. 6.

Example 22

(R)-5-((E)-2-Pyrrolidin-3-ylvinyl)pyrimidine mono-maleate Form I (R)-5-((E)-2-pyrrolidin-3-ylvinyl)pyrimidine free base (189 mg, 1.077 mmol, freshly prepared) was dissolved in acetonitrile (5 ml). The solution was then treated with 1.1 eq. of an maleic acid solution (1M in tetrahydrofuran) at ambient temperature. The mixture was warmed up to 50° C. and cooled down slowly to ambient temperature overnight. The solid obtained was filtered and dried under suction before being analysed by XRPD, and $^1$H-NMR. The XRPD diffractogram of (R)-5-((E)-2-pyrrolidin-3-ylvinyl)pyrimidine mono-maleate Form I is shown in FIG. 7.

Example 23

(R)-5-((E)-2-Pyrrolidin-3-ylvinyl)pyrimidine mono-maleate Form II (R)-5-((E)-2-pyrrolidin-3-ylvinyl)pyrimidine mono-maleate (Form I) was slurried in ethanol and incubated at 50° C./r.t. 4 h-cycle for 48 h. XRPD analysis of the solid showed Form II. The XRPD diffractogram of (R)-5-((E)-2-pyrrolidin-3-ylvinyl)pyrimidine mono-maleate Form II is shown in FIG. 8.

Example 24

(R)-5-((E)-2-Pyrrolidin-3-ylvinyl)pyrimidine mono-oxalate

Oxalic acid (0.516 g, 5.73 mmol) was added as a solid to a stirring, warm solution of (R)-5-((E)-2-pyrrolidin-3-ylvinyl)pyrimidine (1.00 g, 5.70 mmol) in ethanol (10 mL). The salt precipitated upon further warming of the solution. To facilitate stirring, the mixture was diluted with ethanol (6 mL), and the lumps were broken with a spatula. The mixture was cooled to ambient temperature and was left standing overnight. The light-beige powder was filtered, washed with ethanol, and dried in a vacuum oven at 50° C. for 6 h to give 1.40 g (92.3%) of a creamy-white, fluffy powder, mp 149-151° C. $^1$H NMR (DMSO-d$_6$): δ 9.03 (s, 1H), 8.86 (s, 2H), 6.56 (m, 2H), 3.40 (dd, 1H), 3.31 (m, 1H), 3.18 (m, 1H), 3.08 (m, 1H), 2.96 (dd, 1H), 2.15 (m, 1H), 1.80 (m, 1H), $^{13}$C NMR (DMSO-d$_6$): δ 164.90 (C=O of oxalic acid), 156.97, 154.17, 133.66, 130.31, 124.20, 48.70, 44.33, 40.98, 30.42. Elemental analysis: Calculated for $C_{10}H_{13}N_3 \cdot C_2H_2O_4$(C, 54.33%; H, 5.70%, N, 15.84%); Found (C, 54.39%, 54.29%; H, 5.68%, 5.66%; N, 15.68%, 15.66%).

Example 25

(R)-5-((E)-2-Pyrrolidin-3-ylvinyl)pyrimidine hemi-di-p-toluoyl-D-tartarate

Solid di-p-toluoyl-D-tartarate salts was obtained according to the "hemi" salt screening procedure from isopropyl acetate or acetonitrile by evaporation, or by evaporation if isopropyl acetate followed by maturation with tetrahydrofuran or by evaporation of acetonitrile followed by maturation with isopropyl alcohol.

The following procedure was used to make a larger quantity of the salt. (+)-O,O'-Di-p-toluoyl-D-tartaric acid (1.103 g, 2.85 mmol) was added as a solid to a stirring, warm solution of (R)-5-((E)-2-pyrrolidin-3-ylvinyl)pyrimidine free base (1.007 g, 5.74 mmol) in ethanol (10 mL). A few insoluble solids precipitated that failed to dissolve upon heating the mixture to reflux. The light amber solution (with a few fine solids) was stirred for 4-5 h and then allowed to stand at ambient temperature overnight. The precipitation of the salt as a light beige powder was slow. After stirring for 15 days, the solids were filtered, washed with ethanol (5 mL) and dried in a vacuum oven at 50° C. for 21 h to give 1.50 g (71.5%) of an off-white to slightly yellow-tinged powder, mp 178-180° C. $^1$H NMR (DMSO-d$_6$) confirms the 1:0.5 base:acid salt stoichiometry. $^1$H NMR (DMSO-d$_6$): δ 10.30 (broad s, ~1H), 9.02 (s, 1H), 8.80 (s, 2H), 7.87 (d, 2H, —C$_6$H$_4$—, indicating a hemi-salt stoichiometry), 7.27 (d, 2H, —C$_6$H$_4$—, indicating a hemi-salt stoichiometry), 6.40 (dd, 1H), 6.34 (d, 1H), 5.58 (s, 1H, CH(CO$_2$H)—O— of acid moiety, indicating a hemi-salt stoichiometry), 3.21 (dd, 1H), 3.14 (m, 1H), 3.00 (m, 1H), 2.86 (m, 1H), 2.75 (dd, 1H), 2.30 (s, 3H, —CH$_3$ of acid moiety, indicating a hemi-salt stoichiometry), 1.93 (m, 1H), 1.61 (m, 1H).

Example 26

(R)-5-((E)-2-Pyrrolidin-3-ylvinyl)pyrimidine hemi-di-p-benzoyl-D-tartarate (+)-O,O'-Di-benzoyl-D-tartaric acid (1.025 g, 2.72 mmol) was added as a solid to a stirring, warm solution of (R)-5-((E)-2-pyrrolidin-3-ylvinyl)pyrimidine free base (1.003 g, 5.72 mmol) in ethanol (10 mL). The mixture was heated to near reflux on a hot plate, producing a light amber solution. The resulting solution was cooled to ambient temperature and was left standing overnight. Because no solids were present, the solution was slowly evaporated in a fume hood, affording tan-brown, gummy solids. Isopropyl acetate (10 mL) was added and with spatula scraping and stirring, light beige solids are deposited. The mixture was stirred overnight. The solids were filtered, washed with isopropyl acetate (2×5 mL) and dried in a vacuum oven at 50° C. for 24 h to give 1.93 g (95.2%) of an off-white powder, mp 155-160° C. $^1$H NMR (DMSO-$d_6$) confirmed the 1:0.5 base:acid salt stoichiometry. $^1$H NMR (DMSO-$d_6$): δ 10.25 (broad s, ~1H), 9.02 (s, 1H), 9.80 (s, 2H), 7.98 (d, 2H $C_6H_5$—), 7.57 (m, 1H, $C_6H_5$—), 7.48 (m, 2H, $C_6H_5$—), 6.38 (m, 2H), 5.61 (s, 1H, —C$\underline{H}$($CO_2$H)—O— of acid moiety, indicating a hemi-salt stoichiometry), 3.22 (dd, 1H), 3.14 (dt, 1H), 3.00 (dt, 1H), 2.88 (m, 1H), 2.77 (dd, 1H), 1.92 (m, 1H), 1.61 (m, 1H).

Example 27

(R)-5-((E)-2-Pyrrolidin-3-ylvinyl)pyrimidine hemi-di-p-anisoyl-D-tartarate (+)-Di-p-anisoyl-D-tartaric acid (1.199 g) was added as a solid to a stirring, warm solution of (R)-5-((E)-2-pyrrolidin-3-ylvinyl)pyrimidine free base (0.999 g) in ethanol (10 mL). The resulting solution, with a few solids present, was stirred and heated in an attempt to dissolve all solids. The solution became a thick mass. After standing at ambient temperature for 4-5 h, additional ethanol (10 mL) was added. The mixture containing light-beige to cream-colored solids was stirred overnight. The solids were filtered, washed with ethanol (10 mL), and dried in a vacuum oven at 50° C. for 21 h to give 1.91 g (87.3%) of a white powder, mp 173-177° C. $^1$H NMR (DMSO-$d_6$) confirmed the 1:0.5 base:acid salt stoichiometry. $^1$H NMR (DMSO-$d_6$): δ 10.20 (broad s, ~1H), 9.02 (s, 1H), 8.80 (s, 2H), 7.93 (d, 2H, —$C_6H_4$—, indicating a hemi-salt stoichiometry), 7.00 (d, 2H, —$C_6H_4$—, indicating a hemi-salt stoichiometry), 6.40 (dd, 1H), 6.34 (d, 1H), 5.56 (s, 1H, C$\underline{H}$($CO_2$H)—O— of acid moiety, indicating a hemi-salt stoichiometry), 3.76 (s, 3H, —O$CH_3$ of acid moiety, indicating a hemi-salt stoichiometry), 3.22 (dd, 1H), 3.14 (m, 1H), 3.01 (m, 1H), 2.85 (m, 1H), 2.75 (m, 1H), 1.92 (m, 1H), 1.61 (m, 1H).

Example 28

(R)-5-((E)-2-Pyrrolidin-3-ylvinyl)pyrimidine mono-di-p-toluoyl-D-tartarate

Solid di-p-toluoyl-D-tartarate salts were obtained according to the "mono" salt screening procedure from isopropyl acetate or acetonitrile by evaporation.

The following procedure was used to make a larger quantity of the salt. (+)-O,O'-Di-p-toluoyl-D-tartaric acid (2.205 g, 5.71 mmol) was added as a solid to a stirring, warm solution of (R)-5-((E)-2-pyrrolidin-3-ylvinyl)pyrimidine free base (1.000 g, 5.70 mmol) in ethanol (21 mL). Precipitation of the salt was immediate. After gently heating the stirring mixture on a hot plate to near reflux, the resulting mixture was cooled to ambient temperature. The resulting solids were filtered, washed with ethanol (3×5 mL), and dried in a vacuum oven at 50° C. for 13 h to give 3.081 g (96.1%) of a light-beige powder, mp 181-184° C. $^1$H NMR (DMSO-$d_6$) confirmed the 1:1 salt stoichiometry. $^1$H NMR (DMSO-$d_6$): δ 9.60 (broad s, ~1H), 9.03 (s, 1H), 8.82 (s, 2H), 7.83 (d, 4H, —$C_6H_4$—, indicating a mono-salt stoichiometry), 7.27 (d, 4H, —$C_6H_4$—, indicating a mono-salt stoichiometry), 6.44 (d, 2H), 5.62 (s, 2H, C$\underline{H}$($CO_2$H)—O— of acid moiety, indicating a mono-salt stoichiometry), 3.30 (dd, 1H), 3.23 (m, 1H), 3.09 (m, 1H), 2.95 (m, 1H), 2.85 (dd, 1H), 2.33 (6H, —$CH_3$ of acid moiety, indicating a mono-salt stoichiometry), 2.02 (m, 1H), 1.69 (m, 1H).

Example 29

(R)-5-((E)-2-Pyrrolidin-3-Ylvinyl)Pyrimidine Mono-Di-p-Benzoyl-D-Tartarate (+)-O,O'-Di-benzoyl-D-tartaric acid (2.05 g, 5.72 mmol) was added as a solid to a stirring, warm solution of (R)-5-((E)-2-pyrrolidin-3-ylvinyl)pyrimidine free base (0.999 g, 5.69 mmol) in ethanol (21 mL) in a round-bottomed flask, producing a solution. After stirring and further heating, precipitation of the salt occurred in the warm solution. The resulting mixture was cooled to ambient temperature over a two-day weekend. The resulting solids were filtered on a Büchner funnel, washed with ethanol (4×5 mL), and dried in a vacuum oven (air bleed) at 50° C. for 13 h to give 2.832 g (93.0%) of a light-beige to off-white powder, mp 165-171° C. $^1$H NMR (DMSO-$d_6$) confirmed the 1:1 salt stoichiometry. $^1$H NMR (DMSO-$d_6$): δ 9.65 (broad s, ~1H), 9.03 (s, 1H), 9.83 (s, 2H), 7.94 (d, 4H, $C_6H_5$—), 7.60 (m, 2H, $C_6H_5$—), 7.50 (m, 4H, $C_6H_5$—), 6.45 (m, 2H), 5.67 (s, 2H, —C$\underline{H}$($CO_2$H)—O— of acid moiety, indicating a mono-salt stoichiometry), 3.31 (dd, 1H), 3.22 (m, 1H), 3.08 (m, 1H), 2.96 (m, 1H), 2.85 (dd, 1H), 2.01 (m, 1H), 1.69 (m, 1H).

Example 30

(R)-5-((E)-2-Pyrrolidin-3-ylvinyl)pyrimidine mono-(1S)-10-camphorsulfonate (1S)-(+)-10-Camphorsulfonic acid (1.329 g, 5.72 mmol) was added as a solid to a stirring, warm solution of (R)-5-((E)-2-pyrrolidin-3-ylvinyl)pyrimidine free base (1.00 g) in 2-propanol (23 mL, 5.70 mmol) in a round-bottomed flask. Upon cooling to ambient temperature, there was no precipitation of solids. The solution was allowed to stand overnight. Gelatinous material containing white solids was observed. After stirring two days, the mixture was diluted with 2-propanol (10.5 mL) because stirring this jelly-like white mass was difficult. After overnight stirring, the resulting white powder was filtered on a Büchner funnel, washed with 2-propanol (5 mL) (NOTE: The solids appeared to have some solubility in 2-propanol) and dried in a vacuum oven (air bleed) at 50° C. for 6 h to give 1.47 g (63.2%) of a white powder, mp 172-173° C. $^1$H NMR (DMSO-$d_6$) confirms the 1:1 salt stoichiometry. After standing seven days, a second crop of light-beige needles was observed in the crystallization liquors. This material was filtered, washed with 2-propanol (10 mL) and dried in a vacuum oven (air bleed) at 50° C. for 21 h to give 0.245 g of light-beige needles, mp 173-174° C. $^1$H NMR (DMSO-$d_6$): δ 9.03 (s, 1H), 8.87 (s, 2H), 6.57 (m, 2H), 3.41 (dd, 1H) 3.33 (m, 1H, partially masked by $H_2O$), 3.21 (m, 1H), 3.10 (m, 1H), 2.98 (dd, 1H), 2.89 (d, 1H, —$CH_2$— of acid moiety, indicating a mono-salt stoichiometry), 2.64 (m, 1H), 2.41 (d, 1H, —$CH_2$— of acid moiety, indicating a mono-salt stoichiometry), 2.25 (t, 0.5H), 2.20 (t 0.5H), 2.15 (m, 1H), 1.93 (t, 1H), 1.82 (m, 3H), 1.28 (m, 2H, —$CH_2$— of acid moiety, indicating a mono-salt stoichiometry), 1.03 (s, 3H, —$CH_3$ of acid moiety, indicating a mono-salt stoichiometry), 0.73 (s, 3H, —$CH_3$ of acid moiety, indicating a mono-salt stoichiometry).

Example 31

(R)-5-((E)-2-Pyrrolidin-3-ylvinyl)pyrimidine mono-(1R,2S)-(+)-Camphorate (1R,2S)-(+)-Camphoric acid (1.149 g, 5.74 mmol) was added as a solid to a stirring, warm solution of (R)-5-((E)-

2-pyrrolidin-3-ylvinyl)pyrimidine free base (1.00 g, 5.70 mmol) in ethanol (14 mL) in a round-bottomed flask. Upon heating, all solids dissolved, affording a yellow solution. No precipitate forms upon standing at ambient temperature overnight. The solution was concentrated via rotary evaporation to an amber-brown foam that was dried under vacuum at 50° C. (air bleed) for 6 h to give 2.098 g of a viscous, amber oil. Isopropyl acetate (10 mL) was added, and the solution was allowed to stand at ambient temperature overnight. There was some evidence of crystal nucleation in the gummy, red-amber oil. More isopropyl acetate (10 mL) and 2-propanol (20 drops) was added, and the mixture was gently heated and stirred over 48 h. The resulting milky, creamy solids with some orange lumps were broken with a spatula, and the mixture (colorless liquor) was stirred overnight. The off-white solids were filtered on a Büchner funnel, washed with cold isopropyl acetate (10 mL) and dried in a vacuum oven (air bleed) at 50° C. for 21 h to give 2.034 g (94.9%) of an off-white to cream colored powder, mp 157-159° C. $^1$H NMR (DMSO-$d_6$) confirmed the 1:1 salt stoichiometry. $^1$H NMR (DMSO-$d_6$): δ 9.00 (s, 1H), 8.85 (s, 2H), 6.58 (dd, 1H), 6.47 (d, 1H), 3.17 (dd, 1H), 3.08 (m, 1H), 2.97 (m, 1H), 2.92 (dd, 1H) 2.74 (dd, 1H), 2.61 (dd, 1H), 2.30 (sextet, 1H), 2.00 (m, 2H), 1.65 (m, 2H), 1.32 (m, 1H), 1.15 (s, 3H, —CH$_3$ of acid moiety, indicating a mono-salt stoichiometry), 1.07 (s, 3H, —CH$_3$ of acid moiety, indicating a mono-salt stoichiometry), 0.75 (s, 3H, —CH$_3$ of acid moiety, indicating a mono-salt stoichiometry).

Example 32

(R)-5-((E)-2-Pyrrolidin-3-ylvinyl)pyrimidine mono-di-p-anisoyl-D-tartarate (+)-Di-p-anisoyl-D-tartaric acid (2.388 g, 5.71 mmol) was added as a solid to a stirring, warm solution of (R)-5-((E)-2-pyrrolidin-3-ylvinyl)pyrimidine free base (1.008 g, 5.75 mmol) in ethanol (22 mL) in a round-bottomed flask. Precipitation of the salt occurred before all of the (+)-di-p-anisoyl-D-tartaric acid had been added. The salt did not dissolve upon heating, but the appearance of the solids changed, with conversion to a light, fluffy, white powder. The mixture was cooled to ambient temperature and was stirred over 48 h. The resulting solids were filtered on a Büchner funnel, washed with ethanol (5×5 mL) and dried in a vacuum oven (air bleed) at 50° C. for 13 h to give 3.20 g (94.4%) of an off-white to white, chalky powder, mp 173-176° C. $^1$H NMR (DMSO-$d_6$) confirms the 1:1 salt stoichiometry. $^1$H NMR (DMSO-$d_6$): δ 9.65 (broad s, ~1H), 9.03 (s, 1H), 8.82 (s, 2H), 7.89 (d, 4H, —C$_6$H$_4$—, indicating a mono-salt stoichiometry), 7.01 (d, 4H, —C$_6$H$_4$—, indicating a mono-salt stoichiometry), 6.44 (m, 2H), 5.60 (s, 2H, CH(CO$_2$H)—O— of acid moiety, indicating a mono-salt stoichiometry), 3.79 (s, 6H, —OCH$_3$ of acid moiety, indicating a mono-salt stoichiometry), 3.30 (dd, 1H), 3.22 (m, 1H), 3.09 (m, 1H), 2.95 (m, 1H), 2.84 (m, 1H), 2.01 (m, 1H), 1.69 (m, 1H).

Example 33

(R)-5-((E)-2-Pyrrolidin-3-ylvinyl)pyrimidine mono-(R)-(−)-Phencyphos salt (R)-(−)-Phencyphos (1.391 g, 5.77 mmol) was added as a solid to a stirring solution of (R)-5-((E)-2-pyrrolidin-3-ylvinyl)pyrimidine free base (1.006 g, 5.73 mmol) in ethanol (10 mL) in a round-bottomed flask. Most of the solids dissolved upon stirring at ambient temperature, and all solids dissolved with gentle heating. The stirring, amber solution was heated to reflux, cooled to ambient temperature and was allowed to stand overnight. The resulting white, needle-like crystals were filtered on a Büchner funnel, washed with cold ethanol (5 mL) and dried in a vacuum oven (air bleed) at 50° C. for 18 h to give 0.811 g (33.9%) of off-white crystals, mp 197-201° C. $^1$H NMR (DMSO-$d_6$) confirms the 1:1 salt stoichiometry. $^1$H NMR (DMSO-$d_6$): δ 9.81 (broad s, ~1H), 9.02 (s, 1H), 8.85 (s, 2H), 7.27 (m, 5H, C$_6$H$_5$—), 6.56 (dd, 1H), 6.48 (d, 1H), 5.00 (d, 1H, —O—CH— of acid moiety, indicating a mono-salt stoichiometry), 4.00 (d, 1H, —O—CH$_2$— of acid moiety, indicating a mono-salt stoichiometry), 3.48 (dd, 1H, —O—CH$_2$— of acid moiety, indicating a mono-salt stoichiometry), 3.36 (dd, 1H), 3.30 (m, 1H), 3.17 (m, 1H), 3.07 (m, 1H), 2.93 (dd, 1H), 2.12 (m, 1H), 1.78 (m, 1H), 0.79 (s, 3H, —CH$_3$ of acid moiety, indicating a mono-salt stoichiometry), 0.60 (s, 3H, —CH$_3$ of acid moiety, indicating a mono-salt stoichiometry).

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

We claim:
1. A composition comprising a mono-orotate salt of (R)-5-((E)-2-pyrrolidin-3-ylvinyl)pyrimidine, wherein the composition is substantially free of (S)-5-((E)-2-pyrrolidin-3-ylvinyl)pyrimidine.
2. The composition of claim 1, wherein the salt is in crystalline form.
3. The composition of claim 2, wherein the crystalline form is characterized by a powder x-ray diffraction pattern comprising at least one of the following peaks:

| 2θ |
| --- |
| 2.55 ± 0.1° |
| 6.54 ± 0.1° |
| 8.66 ± 0.1° |
| 13.26 ± 0.1° |
| 14.56 ± 0.1° |
| 15.98 ± 0.1° |
| 17.47 ± 0.1° |
| 18.53 ± 0.1° |
| 19.30 ± 0.1° |
| 20.26 ± 0.1° |
| 21.05 ± 0.1° |
| 22.02 ± 0.1° |
| 23.14 ± 0.1° |
| 24.32 ± 0.1° |
| 25.56 ± 0.1° |
| 26.87 ± 0.1° |
| 27.84 ± 0.1° |
| 28.76 ± 0.1° |
| 29.53 ± 0.1°. |

4. The composition of claim 2, wherein the crystalline form is characterized by an XRPD pattern that substantially corresponds to that shown in FIG. 6.
5. A pharmaceutical composition comprising the composition of claim 1 and at least one pharmaceutically acceptable carrier, diluent, or excipient.

6. A method of treating pain in a patient in need thereof comprising administration of an effective amount of the composition of claim 1 to the patient in need thereof.

7. A composition comprising a mono-maleate salt of (R)-5-((E)-2-pyrrolidin-3-ylvinyl)pyrimidine, wherein the composition is substantially free of (S)-5-((E)-2-pyrrolidin-3-ylvinyl)pyrimidine.

8. The composition of claim 7, wherein the salt is in crystalline form.

9. The composition of claim 8, wherein the crystalline form is characterized by a powder x-ray diffraction pattern comprising at least one of the following peaks:

| 2θ |
|---|
| 12.81 ± 0.1° |
| 16.09 ± 0.1° |
| 18.00 ± 0.1° |
| 19.07 ± 0.1° |
| 24.49 ± 0.1° |
| 26.40 ± 0.1° |
| 26.04 ± 0.1° |
| 27.88 ± 0.1°. |

10. The composition of claim 8, wherein the crystalline form is characterized by an XRPD pattern that substantially corresponds to that shown in FIG. 7.

11. The composition of claim 8, wherein the crystalline form is characterized by a powder x-ray diffraction pattern comprising at least one of the following peaks:

| 2θ |
|---|
| 4.31 ± 0.1° |
| 16.56 ± 0.1° |
| 18.29 ± 0.1° |
| 18.78 ± 0.1° |
| 19.64 ± 0.1° |
| 20.27 ± 0.1° |
| 21.02 ± 0.1° |
| 21.46 ± 0.1° |
| 21.90 ± 0.1° |
| 22.43 ± 0.1° |
| 22.86 ± 0.1° |
| 25.40 ± 0.1° |
| 25.73 ± 0.1° |
| 26.15 ± 0.1° |
| 26.56 ± 0.1° |
| 27.40 ± 0.1° |
| 28.59 ± 0.1° |
| 29.57 ± 0.1°. |

12. The composition of claim 8, wherein the crystalline form is characterized by an XRPD pattern that substantially corresponds to that shown in FIG. 8.

13. A pharmaceutical composition comprising the composition of claim 7 and at least one pharmaceutically acceptable carrier, diluent, or excipient.

14. A method of treating pain in a patient in need thereof comprising administration of an effective amount of the composition of claim 7 to the patient in need thereof.

* * * * *